(12) United States Patent
Sheldon et al.

(10) Patent No.: US 11,684,785 B2
(45) Date of Patent: Jun. 27, 2023

(54) DYNAMIC PATIENT-SPECIFIC FILTERING OF AN ACTIVITY SIGNAL WITHIN A BEATING HEART

(71) Applicant: Medtronic, Inc., Minneapolis, MN (US)

(72) Inventors: Todd J. Sheldon, North Oaks, MN (US); Wade M. Demmer, Coon Rapids, MN (US); Karen J. Kleckner, Bradenton, FL (US); Douglas A. Peterson, Apple Valley, MN (US); Paul R. Solheim, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/369,711

(22) Filed: Jul. 7, 2021

(65) Prior Publication Data

US 2021/0330983 A1 Oct. 28, 2021

Related U.S. Application Data

(60) Continuation of application No. 16/718,753, filed on Dec. 18, 2019, which is a continuation of application No. 15/669,091, filed on Aug. 4, 2017, now Pat. No. 10,518,094, which is a division of application No. 14/552,758, filed on Nov. 25, 2014, now Pat. No. 9,724,518.

(51) Int. Cl.
*A61N 1/365* (2006.01)
*A61N 1/36* (2006.01)

(52) U.S. Cl.
CPC ..... *A61N 1/36542* (2013.01); *A61N 1/36128* (2013.01); *A61N 1/36585* (2013.01)

(58) Field of Classification Search
None
See application file for complete search history.

(56) References Cited

U.S. PATENT DOCUMENTS

| 761,162 A | 5/1904 | Gold |
|---|---|---|
| 4,374,382 A | 2/1983 | Markowitz |
| 4,476,868 A | 10/1984 | Thompson |

(Continued)

FOREIGN PATENT DOCUMENTS

| CN | 1819855 A | 8/2006 |
|---|---|---|
| CN | 1838076 A | 9/2006 |

(Continued)

OTHER PUBLICATIONS

Tom Kenny, The Nuts and Bolts of Cardiac Pacing, John Wiley & Sons, Sep. 23, 2011, viewed on Aug. 9, 2021.*

(Continued)

*Primary Examiner* — Unsu Jung
*Assistant Examiner* — James Moss
(74) *Attorney, Agent, or Firm* — Shumaker & Sieffert, P.A.

(57) ABSTRACT

An implantable medical device includes an activity sensor, a pulse generator, and a control module. The control module is configured to determine activity metrics from the activity signal and determine an activity metric value at a predetermined percentile of the activity metrics. The control module sets a lower pacing rate set point based on the activity metric value at the predetermined percentile.

20 Claims, 10 Drawing Sheets

(56) References Cited

U.S. PATENT DOCUMENTS

| | | | |
|---|---|---|---|
| 4,485,813 A * | 12/1984 | Anderson | A61B 5/0215 600/488 |
| 4,940,052 A * | 7/1990 | Mann | A61N 1/36542 607/30 |
| 5,040,534 A * | 8/1991 | Mann | A61N 1/36542 607/19 |
| 5,052,388 A * | 10/1991 | Sivula | A61N 1/36514 607/22 |
| 5,065,759 A * | 11/1991 | Begemann | A61N 1/36585 607/18 |
| 5,074,302 A * | 12/1991 | Poore | A61N 1/36542 607/19 |
| 5,117,824 A | 6/1992 | Keimel et al. | |
| 5,154,170 A | 10/1992 | Bennett et al. | |
| 5,158,078 A | 10/1992 | Bennett et al. | |
| 5,165,404 A | 11/1992 | Andersoon et al. | |
| 5,165,405 A | 11/1992 | Eckwall | |
| 5,172,690 A | 12/1992 | Nappholz et al. | |
| 5,190,034 A | 3/1993 | Sholder | |
| 5,222,493 A | 6/1993 | Sholder | |
| 5,226,413 A | 7/1993 | Bennett et al. | |
| 5,231,986 A | 8/1993 | Bennett | |
| 5,285,780 A | 2/1994 | Tsuji et al. | |
| 5,292,341 A * | 3/1994 | Snell | A61N 1/36585 607/30 |
| 5,304,208 A | 4/1994 | Inguaggiato et al. | |
| 5,312,454 A | 5/1994 | Roline et al. | |
| 5,320,643 A | 6/1994 | Roline et al. | |
| 5,324,310 A | 6/1994 | Greeninger et al. | |
| 5,345,362 A | 9/1994 | Winkler | |
| 5,354,317 A | 10/1994 | Alt | |
| 5,423,867 A | 6/1995 | Poore et al. | |
| 5,425,750 A * | 6/1995 | Moberg | A61N 1/36542 600/595 |
| 5,447,525 A | 9/1995 | Powell et al. | |
| 5,496,351 A | 3/1996 | Plicchi et al. | |
| 5,507,782 A | 4/1996 | Kieval et al. | |
| 5,507,785 A | 4/1996 | Deno | |
| 5,514,162 A * | 5/1996 | Bornzin | A61N 1/36542 607/19 |
| 5,562,711 A * | 10/1996 | Yerich | A61N 1/36585 607/17 |
| 5,593,431 A | 1/1997 | Sheldon | |
| 5,601,615 A | 2/1997 | Markowitz et al. | |
| 5,609,312 A | 3/1997 | Arlton et al. | |
| 5,609,612 A | 3/1997 | Plicchi et al. | |
| 5,628,777 A | 5/1997 | Moberg et al. | |
| 5,674,258 A * | 10/1997 | Henschel | G01P 1/02 607/19 |
| 5,683,432 A | 11/1997 | Goedeke et al. | |
| 5,693,075 A | 12/1997 | Plicchi et al. | |
| 5,720,769 A * | 2/1998 | van Oort | A61N 1/36542 607/17 |
| 5,755,740 A | 5/1998 | Nappholz | |
| 5,766,230 A | 6/1998 | Routh et al. | |
| 5,782,889 A | 7/1998 | Hognelid et al. | |
| 5,885,471 A * | 3/1999 | Ruben | B81B 3/0051 216/33 |
| 5,944,745 A | 8/1999 | Rueter | |
| 5,954,755 A | 9/1999 | Casavant | |
| 6,044,297 A | 3/2000 | Sheldon et al. | |
| 6,055,454 A | 4/2000 | Heemels | |
| 6,389,316 B1 | 5/2002 | Bornzin et al. | |
| 6,449,508 B1 * | 9/2002 | Sheldon | A61N 1/36542 600/595 |
| 6,553,259 B2 | 4/2003 | Mouchawar et al. | |
| 6,772,005 B2 | 8/2004 | Casavant et al. | |
| 6,819,955 B2 | 11/2004 | Levine | |
| 6,950,704 B1 | 9/2005 | Bradley | |
| 7,031,772 B2 | 4/2006 | Condie et al. | |
| 7,076,283 B2 | 7/2006 | Cho et al. | |
| 7,130,690 B2 | 10/2006 | Rueter et al. | |
| 7,280,868 B2 | 10/2007 | Rueter et al. | |
| 7,400,924 B2 | 7/2008 | Rueter | |
| 7,457,666 B2 | 11/2008 | Bohn et al. | |
| 7,532,930 B2 | 5/2009 | Schermeier et al. | |
| 7,761,162 B2 | 7/2010 | Dong et al. | |
| 7,778,696 B2 | 8/2010 | Sathaye | |
| 7,783,355 B2 | 8/2010 | Rueter | |
| 7,818,059 B2 | 10/2010 | Rueter et al. | |
| 7,831,303 B2 | 11/2010 | Rueter et al. | |
| 8,280,509 B2 | 10/2012 | Sathaye | |
| 8,433,409 B2 | 4/2013 | Johnson et al. | |
| 8,532,785 B1 | 9/2013 | Crutchfield et al. | |
| 8,541,131 B2 | 9/2013 | Lund et al. | |
| 8,956,295 B2 | 2/2015 | Ni et al. | |
| 9,452,292 B2 | 9/2016 | Demmer et al. | |
| 9,724,518 B2 | 8/2017 | Sheldon et al. | |
| 10,518,094 B2 | 12/2019 | Sheldon et al. | |
| 2002/0183798 A1 | 12/2002 | Vonk | |
| 2003/0069611 A1 | 4/2003 | Levine | |
| 2003/0078624 A1 | 4/2003 | Carlson et al. | |
| 2003/0078627 A1 | 4/2003 | Casavant et al. | |
| 2003/0083700 A1 | 5/2003 | Hill | |
| 2003/0083712 A1 | 5/2003 | Rueter et al. | |
| 2003/0153956 A1 * | 8/2003 | Park | A61N 1/36585 607/17 |
| 2003/0195579 A1 | 10/2003 | Bradley et al. | |
| 2003/0204214 A1 | 10/2003 | Ferek-Patric | |
| 2004/0030358 A1 | 2/2004 | Rueter et al. | |
| 2004/0088019 A1 | 5/2004 | Rueter et al. | |
| 2004/0260352 A1 | 12/2004 | Rueter et al. | |
| 2005/0015985 A1 | 1/2005 | Dvoskin | |
| 2005/0021095 A1 | 1/2005 | Rueter et al. | |
| 2005/0159785 A1 | 7/2005 | Rueter | |
| 2005/0222630 A1 | 10/2005 | Schermeier et al. | |
| 2005/2045988 | 11/2005 | Miesel | |
| 2006/0155338 A1 | 7/2006 | Mongeon et al. | |
| 2006/0241710 A1 | 10/2006 | Rueter | |
| 2006/0247705 A1 | 11/2006 | Rueter et al. | |
| 2006/0253156 A1 | 11/2006 | Pastore et al. | |
| 2007/0115277 A1 | 5/2007 | Wang et al. | |
| 2008/0195165 A1 | 8/2008 | Stahmann et al. | |
| 2010/0010380 A1 | 1/2010 | Panken et al. | |
| 2010/0010583 A1 | 1/2010 | Panken et al. | |
| 2011/0012759 A1 | 1/2011 | Yin | |
| 2011/0029034 A1 | 2/2011 | Fischer et al. | |
| 2011/0152963 A1 | 6/2011 | Stahmann et al. | |
| 2012/0065524 A1 | 3/2012 | Morren et al. | |
| 2012/0109259 A1 | 5/2012 | Bond et al. | |
| 2012/0172892 A1 | 7/2012 | Grubac et al. | |
| 2012/0245476 A1 | 9/2012 | Skerl et al. | |
| 2013/0035748 A1 | 2/2013 | Bonner et al. | |
| 2013/0079861 A1 | 3/2013 | Reinert et al. | |
| 2013/0090702 A1 | 4/2013 | Mongeon et al. | |
| 2013/0116602 A1 | 5/2013 | Van Den Heuvel et al. | |
| 2013/0150911 A1 | 6/2013 | Perschbacher et al. | |
| 2013/0211205 A1 | 8/2013 | Havel et al. | |
| 2013/0289652 A1 | 10/2013 | Skelton et al. | |
| 2014/0200691 A1 | 7/2014 | Lee et al. | |
| 2015/0173655 A1 | 6/2015 | Demmer et al. | |
| 2015/0217119 A1 | 8/2015 | Nikolski et al. | |
| 2015/0238769 A1 | 8/2015 | Demmer et al. | |
| 2016/0144191 A1 | 5/2016 | Sheldon et al. | |
| 2017/0113051 A1 | 4/2017 | Sheldon et al. | |
| 2020/0121931 A1 | 4/2020 | Sheldon et al. | |

FOREIGN PATENT DOCUMENTS

| | | |
|---|---|---|
| CN | 102526879 A | 7/2012 |
| EP | 0259658 A2 | 3/1988 |
| EP | 1116495 A2 | 7/2001 |
| EP | 2239007 A1 | 10/2010 |
| WO | 2004041086 A1 | 5/2004 |

OTHER PUBLICATIONS (PCT/US2014/067337) PCT Notification of Transmittal of the International Search Report and the Written Opinion of the International Searching Authority, dated Feb. 20, 2015, 13 pages.

(56) References Cited

OTHER PUBLICATIONS (PCT/US2014/070598) PCT Notification of Transmittal of the International Search Report and the Written Opinion of the International Searching Authority, dated Mar. 16, 2015, 11 pages.
(PCT/US2015/013729) PCT Notification of Transmittal of the International Search Report and the Written Opinion of the International Searching Authority, dated Apr. 13, 2015, 9 pages.
(PCT/US2015/027055) PCT Notification of Transmittal of the International Search Report and the Written Opinion of the International Searching Authority, dated Sep. 30, 2015, 9 pages.
(PCT/US2015/062137) Invitation to Pay Additional fees and, where applicable, protest fee, dated Mar. 1, 2016, 8 pages.
(PCT/US2015/062137) PCT Notification of Transmittal of the International Search Report and the Written Opinion of the International Searching Authority, dated Jun. 6, 2016, 18 pages.
(PCT/US2016/049573) PCT Notification of Transmittal of the International Search Report and the Written Opinion of the International Searching Authority, dated Nov. 28, 2016, 10 pages.
Communication pursuant to Rule 164(2)(b) and Article 94(3) EPC from European Application No. 15804661.5, dated Jan. 11, 2021, 12 pp.
Sheldon et al., "Implantable Medical Device With an Activity Sensor for Rate-Adaptive Pacing", Chinese Patent Application No. 201580073460.X, First Office Action, dated Dec. 4, 2019, 10 pages.
Telectronics Pacing Systems, META DDDR, Model 1254, Physician Manual (55 pages), "Multiprogrammable, Minute Ventilation, Rate Responsive Pulse Generator with Telemetry", 1993.
Telectronics Pacing Systems, META DDOR, Model 1256, Physician Manual, Chapter 8 (46 pages), "Multiprogrammable Minute Ventilation Rate Responsive Pulse Generator with Telemetry", Authorized 1993.
Prosecution History from U.S. Appl. No. 14/552,658, dated Apr. 16, 2015 through Mar. 31, 2017, 156 pp.
Prosecution History from U.S. Appl. No. 15/669,091, dated Feb. 8, 2019 through Aug. 27, 2019, 40 pp.
Prosecution History from U.S. Appl. No. 16/718,753, dated Feb. 11, 2020 through Jul. 26, 2021, 89 pp.
Office Action from U.S. Appl. No. 16/718,753, dated Sep. 22, 2021, 25 pp.
Advisory Action from U.S. Appl. No. 16/718,753, dated Aug. 13, 2021, 3 pp.
Response to Office Action dated Sep. 22, 2021, from U.S. Appl. No. 16/718,753, filed Dec. 20, 2021, 16 pp.
Final Office Action from U.S. Appl. No. 16/718,753, dated Apr. 26, 2022, 29 pp.
Office Action from U.S. Appl. No. 16/718,753 dated Oct. 6, 2022, 27 pp.
Advisory Action from U.S. Appl. No. 16/718,753 dated Jul. 19, 2022, 3 pp.
Response to Final Office Action dated Apr. 26, 2022 from U.S. Appl. No. 16/718,753, filed Jun. 27, 2022, 18 pp.
Appeal Brief from U.S. Appl. No. 16/718,753, filed Mar. 31, 2023, 41 pp.
Notice of Appeal from U.S. Appl. No. 16/718,753, filed Jan. 6, 2023, 1 pp.

\* cited by examiner

DYNAMIC PATIENT-SPECIFIC FILTERING OF AN ACTIVITY SIGNAL WITHIN A BEATING HEART

This application is a continuation of U.S. patent application Ser. No. 16/718,753, filed Dec. 18, 2019, which is a continuation of U.S. patent application Ser. No. 15/669,091, filed Aug. 4, 2017, now U.S. Pat. No. 10,518,094, which is a divisional of U.S. application Ser. No. 14/552,758, filed Nov. 25, 2014, now U.S. Pat. No. 9,724,518. The entire content of each of these applications is incorporated herein by reference.

TECHNICAL FIELD

The disclosure relates to implantable medical devices having an activity sensor for monitoring patient activity and an associated method for filtering heart activity from the activity sensor signal.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. Other IMDs may incorporate electrodes and/or other sensors along or within a housing of the IMD that encloses circuitry and electronic components of the IMD.

IMDs may deliver therapy to and/or monitor conditions of a variety of organs, nerves, muscle or tissue, such as the heart, brain, stomach, spinal cord, pelvic floor, or the like. Some IMDs, such as cardiac pacemakers, monitor a patient's heart activity and provide therapeutic electrical stimulation to the heart of the patient via electrodes coupled to the pacemaker. The electrical stimulation provided by the IMD may include signals such as pacing pulses to address abnormal cardiac rhythms such as bradycardia.

In some cases, the IMD senses a signal representative of the metabolic demand of the patient in order to provide cardiac pacing at a rate intended to meet the metabolic demand of the patient. For example, an indication of the patient's physical activity level may be determined from an accelerometer signal correlated to physical activity in order provide rate responsive pacing to dynamically maintain a heart rate that meets the metabolic demand of the patient.

SUMMARY

In general, the disclosure is directed to techniques for controlling cardiac pacing that avoid increasing the pacing rate due to heart activity falsely detected as physical activity of the patient. A pacemaker operating in accordance with the techniques disclosed herein determines a lower pacing rate set point based on an activity sensor signal. The lower rate set point establishes a level of an activity metric determined from the activity sensor signal below which sensed activity is expected to be due largely to heart motion and not an indication of increased metabolic demand due to physical activity. The pacing rate is increased above a lower pacing rate only when the activity metric is above the lower rate set point.

In one example, the disclosure provides a method comprising sensing an activity signal correlated to a metabolic demand of the patient, determining a first plurality of activity metrics from the activity signal, determining an activity metric value at a predetermined percentile of the first plurality of activity metrics, setting a lower rate set point based on the activity metric value at the predetermined percentile, determining a next activity metric from the activity signal and delivering cardiac pacing at a lower base pacing rate in response to at least the next activity metric being less than or equal to the lower rate set point.

In another example, the disclosure provides an implantable medical device (IMD) comprising an activity sensor configured to produce a signal correlated to a metabolic demand of a patient, a pulse generator configured to generate and deliver pacing pulses to a patient's heart via a pair of electrodes coupled to the implantable medical device, and a control module coupled to the pulse generator and the activity sensor. The control module is configured to determine a plurality of activity metrics from the activity signal, determine an activity metric value at a predetermined percentile of the plurality of activity metrics, set a lower rate set point based on the activity metric value at the predetermined percentile, determine a next activity metric from the activity signal, and control the pulse generator to deliver cardiac pacing pulses at a lower base pacing rate in response to at least the next activity metric being less than or equal to the lower rate set point.

In another example, the disclosure provides a non-transitory, computer readable storage medium storing a set of instructions that, when executed by a control module of an implantable medical device, cause the device to sense an activity signal correlated to a metabolic demand of the patient, determine a plurality of activity metrics from the activity signal, determine an activity metric value at a predetermined percentile of the plurality of activity metrics, set a lower rate set point based on the activity metric value at the predetermined percentile, determine a next activity metric from the activity signal, and deliver cardiac pacing pulses at a lower base pacing rate in response to at least the next activity metric being less than or equal to the lower rate set point.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

An implantable medical device (IMD) system is disclosed herein that includes an intracardiac pacemaker configured to be implanted wholly in a chamber of a patient's heart and including a patient activity sensor for producing a signal correlated to patient activity. In various examples, the IMD system may include an atrial intracardiac pacemaker, a ventricular intracardiac pacemaker or both an atrial and ventricular intracardiac pacemaker that do not require transvenous leads. The activity sensor signal is used for establishing a sensor-indicated pacing rate to provide rate-responsive cardiac pacing that is automatically adjusted to meet the patient's metabolic demand. The activity sensor, e.g., an accelerometer, included in the intracardiac pacemaker is subjected to heart motion such that the activity sensor signal includes heart motion signals. Techniques disclosed herein enable the intracardiac pacemaker to adjust the pacing rate based on patient activity and avoid adjusting the pacing rate based on heart motion artifact contained in the accelerometer signal.

Figure 1:
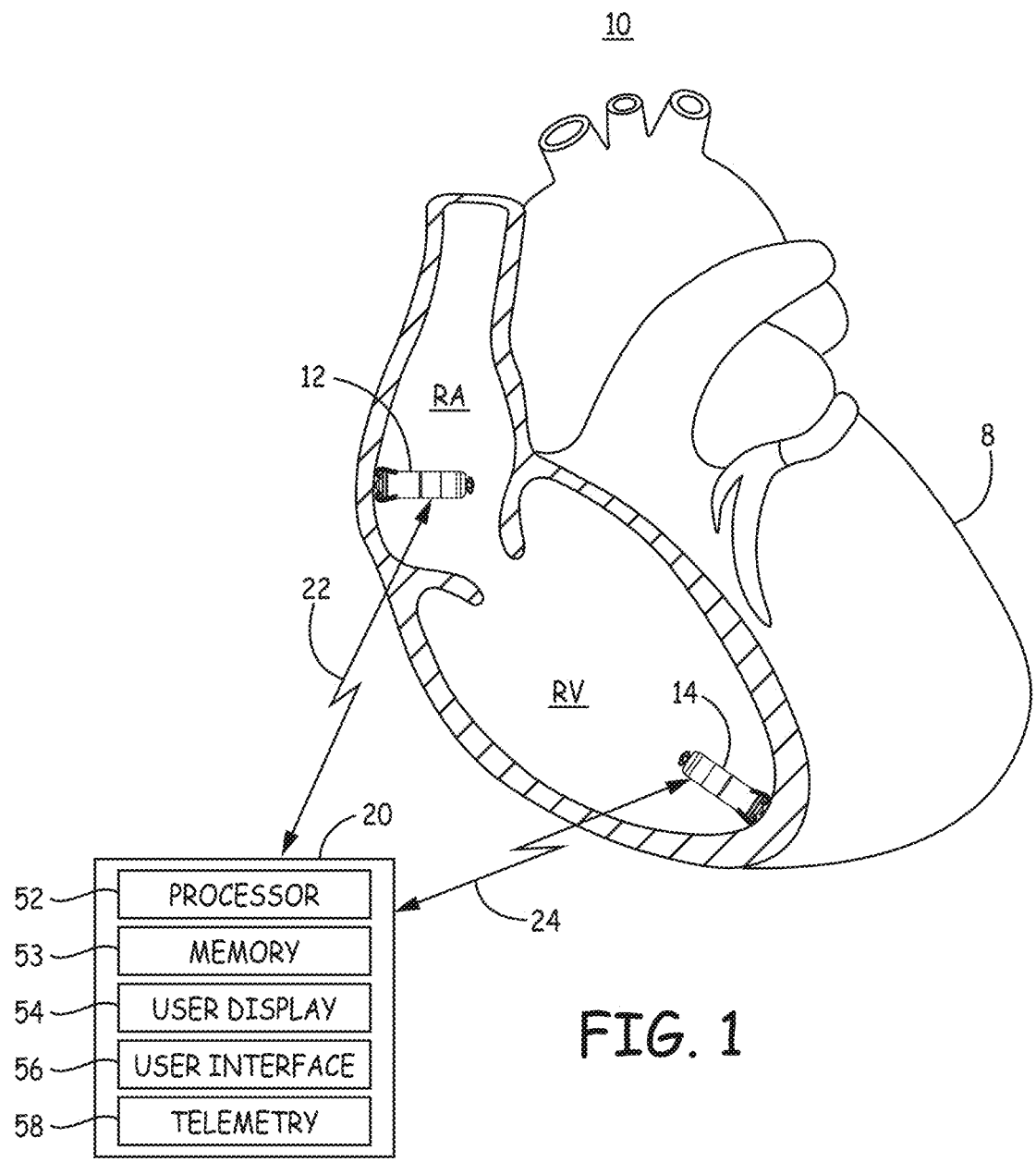
FIG. 1 is a conceptual diagram illustrating an intracardiac pacing system that may be used to sense cardiac electrical signals and provide therapy to a patient's heart.

FIG. 1 is a conceptual diagram illustrating an intracardiac pacing system 10 that may be used to sense cardiac electrical signals and provide therapy to a patient's heart 8. IMD system 10 includes a right ventricular (RV) intracardiac pacemaker 14 and a right atrial (RA) intracardiac pacemaker 12. A cardiac pacing system employing the techniques disclosed herein is not limited to a system including both a RA pacemaker 12 and a RV pacemaker 14. Rather, a cardiac pacing system employing the disclosed techniques may include one or more pacemakers configured to be positioned inside or outside heart 8 and including a motion-based patient activity sensor that is subjected to the motion of the beating heart 8.

In the example shown, pacemakers 12 and 14 are transcatheter intracardiac pacemakers adapted for implantation wholly within a heart chamber, e.g., wholly within the RV, wholly within the left ventricle (LV), wholly within the RA or wholly within the left atrium (LA) of heart 8. RA pacemaker 12 is shown positioned along an endocardial wall of the RA, e.g., along the RA lateral wall or RA septum. RV pacemaker 14 is shown positioned along an endocardial wall of the RV, e.g., near the RV apex. The techniques disclosed herein, however, are not limited to the pacemaker locations shown in the example of FIG. 1 and other relative locations within the respective heart chambers are possible.

Pacemakers 12 and 14 are reduced in size compared to subcutaneously implanted pacemakers and are generally cylindrical in shape to enable transvenous implantation via a delivery catheter. In other examples, pacemakers 12 and 14 may be positioned at any other location inside or outside heart 8, including epicardial locations. For example, pacemaker 12 may be positioned outside or within the right atrium or left atrium to provide respective right atrial or left atrial pacing. Pacemaker 14 may be positioned outside or within the right ventricle or left ventricle to provide respective right ventricular or left ventricular pacing.

Pacemakers 12 and 14 are each capable of producing electrical stimulation pulses, i.e., pacing pulses, delivered to heart 8 via one or more electrodes on the outer housing of the pacemaker. RA pacemaker 12 is configured to sense an intracardiac electrogram (EGM) signal in the RA using the housing based electrodes and deliver RA pacing pulses. RV pacemaker 14 is configured to sense an EGM signal in the RV using housing based electrodes and deliver RV pacing pulses.

Pacemakers 12 and 14 are each capable of bidirectional wireless communication with an external device 20. External device 20 is often referred to as a "programmer" because it is typically used by a physician, technician, nurse, clinician or other qualified user for programming operating parameters in pacemakers 12 and 14. External device 20 may be located in a clinic, hospital or other medical facility. External device 20 may alternatively be embodied as a home monitor or a handheld device that may be used in a medical facility, in the patient's home, or another location. Operating parameters, such as sensing and therapy delivery control parameters, may be programmed into pacemakers 12 and 14 using external device 20. Aspects of external device 20 may generally correspond to the external programming/monitoring unit disclosed in U.S. Pat. No. 5,507,782 (Kieval, et al.), hereby incorporated herein by reference in its entirety.

External device 20 includes a processor 52, memory 53, user display 54, user interface 56 and telemetry module 58. Processor 52 controls external device operations and processes data and signals received from pacemakers 12 and 14. According to techniques disclosed herein, processor 52 may be used to program initial set points of a sensor indicated rate transfer function and a patient activity percentile used in controlling rate responsive cardiac pacing based on an activity sensor signal. Processor 52 may provide user display 54 with data for generating a graphical user interface to a user for selecting and programming control parameters used in controlling rate responsive pacing by pacemaker 12 or pacemaker 14 as well as other pacemaker functions.

External device 20 may display other data and information relating to pacemaker 12 or 14 functions to a user for reviewing pacemaker operation and programmed parameters as well as EGM signals or other physiological data that are retrieved from pacemakers 12 and 14 during an interrogation session. User interface 56 may include a mouse, touch screen, keyboard and/or keypad to enable a user to interact with external device 20 to initiate a telemetry session with pacemakers 12 and 14 for retrieving data from and/or transmitting data to pacemakers 12 and 14 for selecting and programming desired sensing and therapy delivery control parameters.

Telemetry module 58 is configured for bidirectional communication with an implantable telemetry module included in pacemakers 12 and 14. Telemetry module 58 establishes a wireless radio frequency (RF) communication link 22 with RA pacemaker 12 and wireless RF communication link 24 with RV pacemaker 14 using a communication protocol that appropriately addresses the targeted pacemaker 12 or 14. An example RF telemetry communication system that may be implemented in system 10 is generally disclosed in U.S. Pat.

No. 5,683,432 (Goedeke, et al.), hereby incorporated herein by reference in its entirety. Telemetry module 58 is configured to operate in conjunction with processor 52 for sending and receiving data relating to pacemaker functions via communication link 22 or 24. Communication links 22 and 24 may be established between respective RA pacemaker 12 and RV pacemaker 14 and external device 20 using a radio frequency (RF) link in the Medical Implant Communication Service (MICS) band, Medical Data Service (MEDS) band, BLUETOOTH® or Wi-Fi.

Telemetry module 58 may be capable of bi-directional communication with pacemakers 12 and 14 over a wide range of distances, e.g., up to approximately 10 meters. In other examples, telemetry communication may require the use of a programming head placed in proximity of RA pacemaker 12 or RV pacemaker 14 to facilitate data transfer. It is contemplated that external device 20 may be in wired or wireless connection to a communications network via telemetry module 58 for transferring data to a remote database or computer to allow remote management of the patient 12.

Figure 2A:
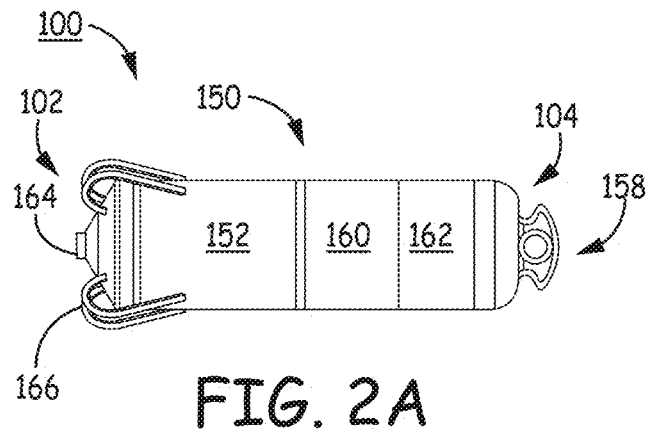
FIG. 2A is a conceptual diagram of an intracardiac pacemaker that may correspond to the right atrial pacemaker or the right ventricular pacemaker shown in FIG. 1.

FIG. 2A is a conceptual diagram of an intracardiac pacemaker 100 that may correspond to RA pacemaker 12 or RV pacemaker 14 shown in FIG. 1. Pacemaker 100 includes electrodes 162 and 164 spaced apart along the housing 150 of pacemaker 100 for sensing cardiac EGM signals and delivering pacing pulses. Electrode 164 is shown as a tip electrode extending from a distal end 102 of pacemaker 100, and electrode 162 is shown as a ring electrode along a mid-portion of housing 150, for example adjacent proximal end 104. Distal end 102 is referred to as "distal" in that it is expected to be the leading end as it advanced through a delivery tool, such as a catheter, and placed against a target pacing site.

Electrodes 162 and 164 form a cathode and anode pair for bipolar cardiac pacing and sensing. Electrodes 162 and 164 may be positioned on or as near as possible to respective proximal and distal ends 104 and 102 to increase the inter-electrode spacing between electrodes 162 and 164.

In alternative embodiments, pacemaker 100 may include two or more ring electrodes, two tip electrodes, and/or other types of electrodes exposed along pacemaker housing 150 for delivering electrical stimulation to heart 8 and sensing EGM signals. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 100 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. In other examples, the entirety of the housing 150 may function as an electrode instead of providing a localized electrode such as electrode 162. Alternatively, electrode 162 may be electrically isolated from the other portions of the housing 150.

The housing 150 includes a control electronics subassembly 152, which houses the electronics for sensing cardiac signals, producing pacing pulses and controlling therapy delivery and other functions of pacemaker 100. Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 100 may include a set of fixation tines 166 to secure pacemaker 100 to patient tissue, e.g., by interacting with the ventricular trabeculae. Fixation tines 166 are configured to anchor pacemaker 100 to position electrode 164 in operative proximity to a targeted tissue for delivering therapeutic electrical stimulation pulses. Numerous types of active and/or passive fixation members may be employed for anchoring or stabilizing pacemaker 100 in an implant position. Pacemaker 100 may include a set of fixation tines as disclosed in commonly-assigned, pre-grant publication U.S. 2012/0172892 (Grubac, et al.), hereby incorporated herein by reference in its entirety.

Pacemaker 100 may further include a delivery tool interface 158. Delivery tool interface 158 may be located at the proximal end 104 of pacemaker 100 and is configured to connect to a delivery device, such as a catheter, used to position pacemaker 100 at an implant location during an implantation procedure, for example within a heart chamber.

A reduced size of pacemaker 100 enables implantation wholly within a heart chamber. In FIG. 1, RA pacemaker 12 and RV pacemaker 14 may have different dimensions. For example, RA pacemaker 12 may be smaller in volume than pacemaker 14, e.g., by reducing battery size, to accommodate implantation in the smaller heart chamber. As such, it is recognized that pacemaker 100 may be adapted in size, shape, electrode location or other physical characteristics according to the heart chamber or location in which it will be implanted.

Figure 2B:
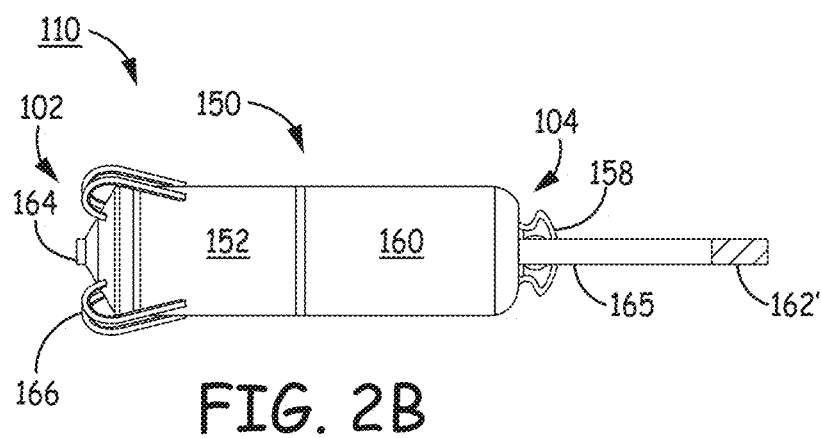
FIG. 2B is a conceptual diagram of an alternative embodiment of an intracardiac pacemaker.

FIG. 2B is a conceptual diagram of an alternative embodiment of an intracardiac pacemaker 110. Pacemaker 110 includes housing 150, control assembly 152, battery assembly 160, fixation member 166 and electrode 164 along a distal end 102, and may include a delivery tool interface 158 along the proximal end 104 as described above in conjunction with FIG. 2A. Pacemaker 110 is shown to include an electrode 162' extending away from housing 150 along an extender 165. As such, instead of carrying a pair of electrodes along the housing 150, which limits the maximum possible inter-electrode spacing, an extender 165 may be coupled to the housing 150 using necessary electrical feedthroughs for positioning an electrode 162' at an increased inter-electrode distance from distal tip electrode 164.

Figure 2C:
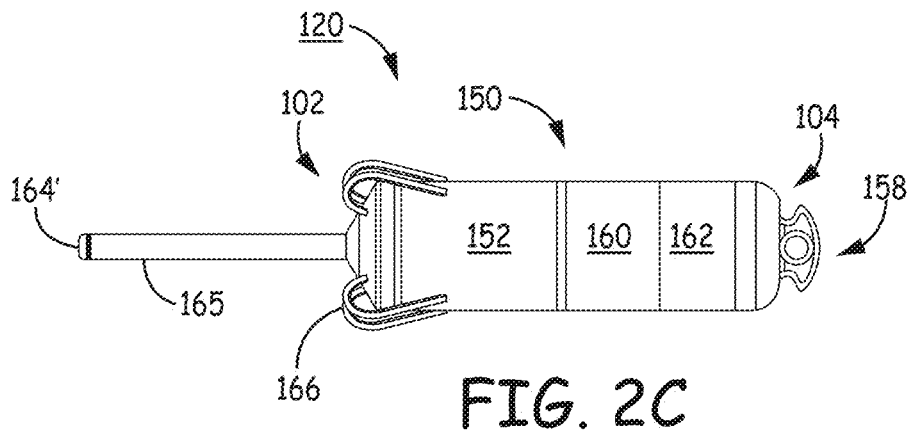
FIG. 2C is a conceptual diagram of yet another embodiment of an intracardiac pacemaker.

FIG. 2C is a conceptual diagram of an alternative embodiment of intracardiac pacemaker 120 having extender 165 coupled to the distal end 102 of pacemaker housing 150 to extend distal electrode 164' away from electrode 162 positioned along housing 150 near or at proximal end 104. Extender 165 shown in FIGS. 2B and 2C is an insulated electrical conductor that electrically couples electrode 162' (FIG. 2B) or electrode 164' (FIG. 2C) to pacemaker circuitry via an electrical feedthrough crossing housing 150. Pacemaker 120 having an insulated, electrically conductive extender 165 for increasing the inter-electrode spacing may correspond generally to the implantable device and flexible conductor disclosed in commonly-assigned, pre-grant U.S. Publication No. 2013/0035748 (Bonner, et al.), hereby incorporated herein by reference in its entirety.

In the examples shown in FIGS. 2A, 2B and 2C, an activity sensor for producing a signal correlated to patient activity may be enclosed in control electronics assembly 152. In other examples, an activity sensor may be located along extender 165 or any other portion of housing 150. The activity sensor may be embodied as a piezoelectric accelerometer in some examples.

Figure 3:
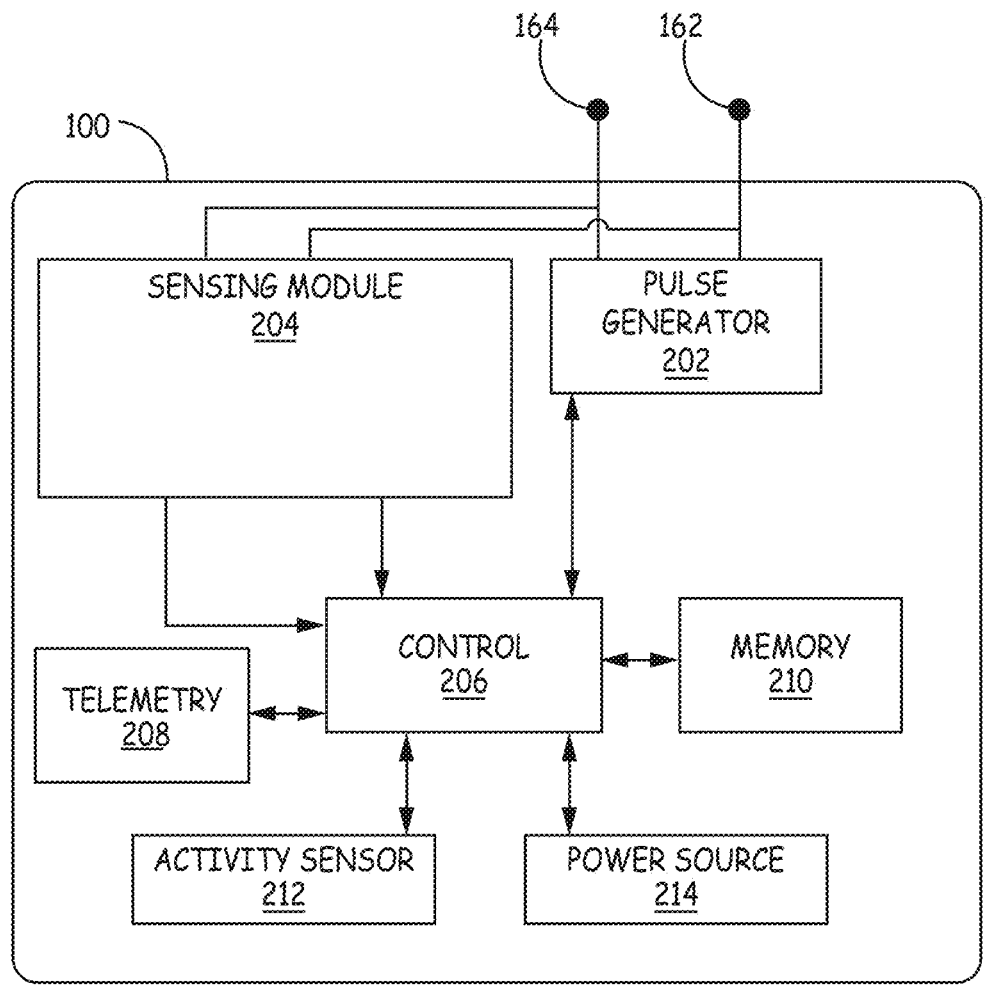
FIG. 3 is a functional block diagram of an example configuration of the intracardiac pacemaker shown in FIG. 2A.

FIG. 3 is a functional block diagram of an example configuration of pacemaker 100 shown in FIG. 2A. Pacemaker 100 includes a pulse generator 202, a sensing module 204, a control module 206, memory 210, telemetry module 208 and a power source 214. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality. Each of RA pacemaker 12 and RV pacemaker 14 may include similar modules as represented by the pacemaker 100 shown in FIG. 3; however it is understood that the modules are configured differently as needed to perform the functionality of the separate RA and RV pacemakers 12 and 14.

For example, when pacemaker 100 is configured to operate as RV pacemaker 14, control module 206 is configured to set various ventricular pacing escape intervals used to control delivery of ventricular pacing pulses. When pacemaker 100 is embodied as RA pacemaker 12, control module 206 is configured to set atrial pacing escape intervals to control delivery of RA pacing pulses.

The functions attributed to pacemaker 100 herein may be embodied as one or more processors, controllers, hardware, firmware, software, or any combination thereof. Depiction of different features as specific circuitry or modules is intended to highlight different functional aspects and does not necessarily imply that such functions must be realized by separate hardware or software components or by any particular architecture. Rather, functionality associated with one or more modules, processors, or circuits may be performed by separate hardware or software components, or integrated within common hardware or software components. For example, pacing control operations performed by pacemaker 100 may be implemented in control module 206 executing instructions stored in associated memory 210 and relying on input from sensing module 204.

Pulse generator 202 generates electrical stimulation pulses that are delivered to heart tissue via electrodes 162 and 164. Electrodes 162 and 164 may be housing-based electrodes as shown in FIG. 2A, but one or both electrodes 162 and 164 may alternatively be carried by an insulated, electrical conductor extending away from the pacemaker housing as described in conjunction with FIGS. 2B and 2C.

Pulse generator 202 may include one or more capacitors and a charging circuit to charge the capacitor(s) to a programmed pacing pulse voltage. At appropriate times, as controlled by a pace timing and control module included in control module 206, the capacitor is coupled to pacing electrodes 162 and 164 to discharge the capacitor voltage and thereby deliver the pacing pulse. Pacing circuitry generally disclosed in the above-incorporated U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 100 for charging a pacing capacitor to a predetermined pacing pulse amplitude under the control of control module 206 and delivering a pacing pulse.

Control module 206 controls pulse generator 202 to deliver a pacing pulse in response to expiration of a pacing escape interval according to programmed therapy control parameters stored in memory 210. The pace timing and control module included in control module 206 may include an escape interval timer that is set to a pacing escape interval used for controlling the timing of pacing pulses relative to a paced or sensed event. Upon expiration of a pacing escape interval, a pacing pulse is delivered. If a cardiac event is sensed during the pacing timing interval by sensing module 204, the scheduled pacing pulse may be inhibited, and the pacing escape interval may be reset to a new time interval. As described below, control module 206 uses a signal from activity sensor 212 for determining a sensor-indicated rate (SIR) used to control the rate of pacing pulse delivery. For example, an escape interval timer included in control module 206 may be set to a pacing escape interval corresponding to a SIR, and the pacing escape interval may be adjusted as the SIR changes in response to the activity sensor signal.

Sensing module 204 receives cardiac EGM signals developed across electrodes 162 and 164. A cardiac event may be sensed by sensing module 204 when the EGM signal crosses a sensing threshold, which may be an auto-adjusting sensing threshold. In response to a sensing threshold crossing, sensing module 204 passes a sensed event signal to control module 206 for use in controlling the timing of pacing pulses.

Memory 210 may include computer-readable instructions that, when executed by control module 206, cause control module 206 to perform various functions attributed throughout this disclosure to pacemaker 100. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 stores timing intervals, counters, or other data used by control module 206 to control the delivery of pacing pulses by pulse generator 202. For example, memory 210 may store set points and slope relationships used in determining the SIR based on the signal from activity sensor 212 received by control module 206.

Activity sensor 212 may be embodied as a piezoelectric accelerometer for producing a signal correlated to patient body motion. The use of an accelerometer in an intracardiac device for obtaining a patient activity signal is generally disclosed in U.S. patent application Ser. No. 14/174,514 filed on Feb. 6, 2014 (Nikolski, et al.), incorporated herein by reference in its entirety. The use of a patient activity signal for providing rate-responsive pacing is generally disclosed in U.S. Pat. No. 7,031,772 (Condie, et al.), incorporated herein by reference in its entirety.

Control module 206 receives an activity signal from activity sensor 212 and determines an activity metric from the signal at a desired frequency for use in determining a sensor-indicated pacing rate. The sensor-indicated rate (SIR) may vary between a programmed lower rate (LR) during periods of rest and a programmed maximum upper pacing rate during periods of maximum exertion. The SIR may be controlled according to a SIR transfer function as described below, which may include different rates of change of the SIR over different ranges of the activity metric.

In some examples, the activity metric is determined as an activity count. In these instances, control module 206 includes a counter to track the activity count as the number of times the signal from activity sensor 212 crosses a threshold during an activity count interval, for example a 2-second interval. The count at the end of each activity count interval is correlated to patient body motion during the activity count interval and is therefore correlated to patient metabolic demand. The threshold applied to the activity sensor signal, which when crossed by the activity sensor signal causes the activity count to be increased, may be a default or programmable threshold or may be an automatically adjusted threshold. Methods for obtaining an activity count over an n-second interval and for adjusting the activity sensor signal threshold used for obtaining the activity count are generally disclosed in commonly-assigned U.S. Pat. No. 5,720,769 (van Oort), incorporated herein by reference in its entirety.

The activity counts determined over a monitoring interval are used by control module 206 for determining an activity count below which the SIR will remain at the programmed LR. This activity count is referred to herein as the "LR set point." An activity count that is greater than the LR set point results in a SIR greater than the lower rate and determined according to a SIR transfer function. An activity count equal to or less than the LR set point results in a SIR equal to the programmed LR.

In other examples, an activity metric may be obtained from the activity sensor signal by integrating or summing activity signal sample points over an activity count interval, e.g., a two-second interval though longer or shorter intervals of time may be used for determining an activity metric. The activity metrics accumulated over an adjustment interval are used to determine the LR set point. Activity metrics accumulated over a monitoring interval after the adjustment interval may be used to update the LR set point.

The techniques described herein are applicable to an activity sensor that is sensitive to patient body motion but produce a sensor signal that results in a non-zero activity metric when the patient is at rest, e.g., due to heart activity. The techniques may be applied to other activity sensor signals that produce a non-zero activity metric when the patient is resting due to heart or other body motion that is not a consequence of physical activity or increased metabolic demand.

Other types of activity sensors may produce a signal correlated to respiratory activity, such as minute ventilation, blood or tissue oxygen saturation, or another indication of the patient's body motion or physical activity. Other types of activity sensors may be used for providing control module 206 with a signal correlated to metabolic demand. Various examples of other types of implantable sensors that may be implemented with a rate responsive pacemaker for controlling pacing rate based on metabolic demand are generally described in U.S. Pat. No. 5,755,740 (Nappholz), U.S. Pat. No. 5,507,785 (Deno), and U.S. Pat. No. 5,312,454 (Roline). The techniques disclosed herein may be implemented in conjunction with any type of activity sensor that has a tendency to produce a signal that includes cardiac activity and therefore indicates a non-zero patient activity level due to cardiac activity even in the absence of actual physical activity or exertion by the patient.

Pacemaker 100 may further include one or more other physiological sensors for monitoring the patient, such as a pressure sensor, an acoustical sensor, an oxygen sensor, or any other implantable physiological sensor. In other examples, activity sensor 212 may be implemented as a three-dimensional accelerometer and used for detecting changes in patient body posture in addition to monitoring patient activity. A multi-dimensional accelerometer for detecting patient posture changes is generally disclosed in in U.S. Pat. No. 5,593,431 (Sheldon), hereby incorporated herein by reference in its entirety.

Power source 214 provides power to each of the other modules and components of pacemaker 100 as required. Control module 206 may execute power control operations to control when various components or modules are powered to perform various pacemaker functions. Power source 214 may include one or more energy storage devices, such as one or more rechargeable or non-rechargeable batteries. The connections between power source 214 and other pacemaker modules and components are not shown in FIG. 3 for the sake of clarity.

Telemetry module 208 includes a transceiver and associated antenna for transferring and receiving data from external device 20 via a radio frequency (RF) communication link as described above. Pacemaker 100 may receive pacing and sensing control parameter values that are stored in memory 210 and accessed by control module 206 via programming commands received by telemetry module 208 from external device 20.

Figure 4:
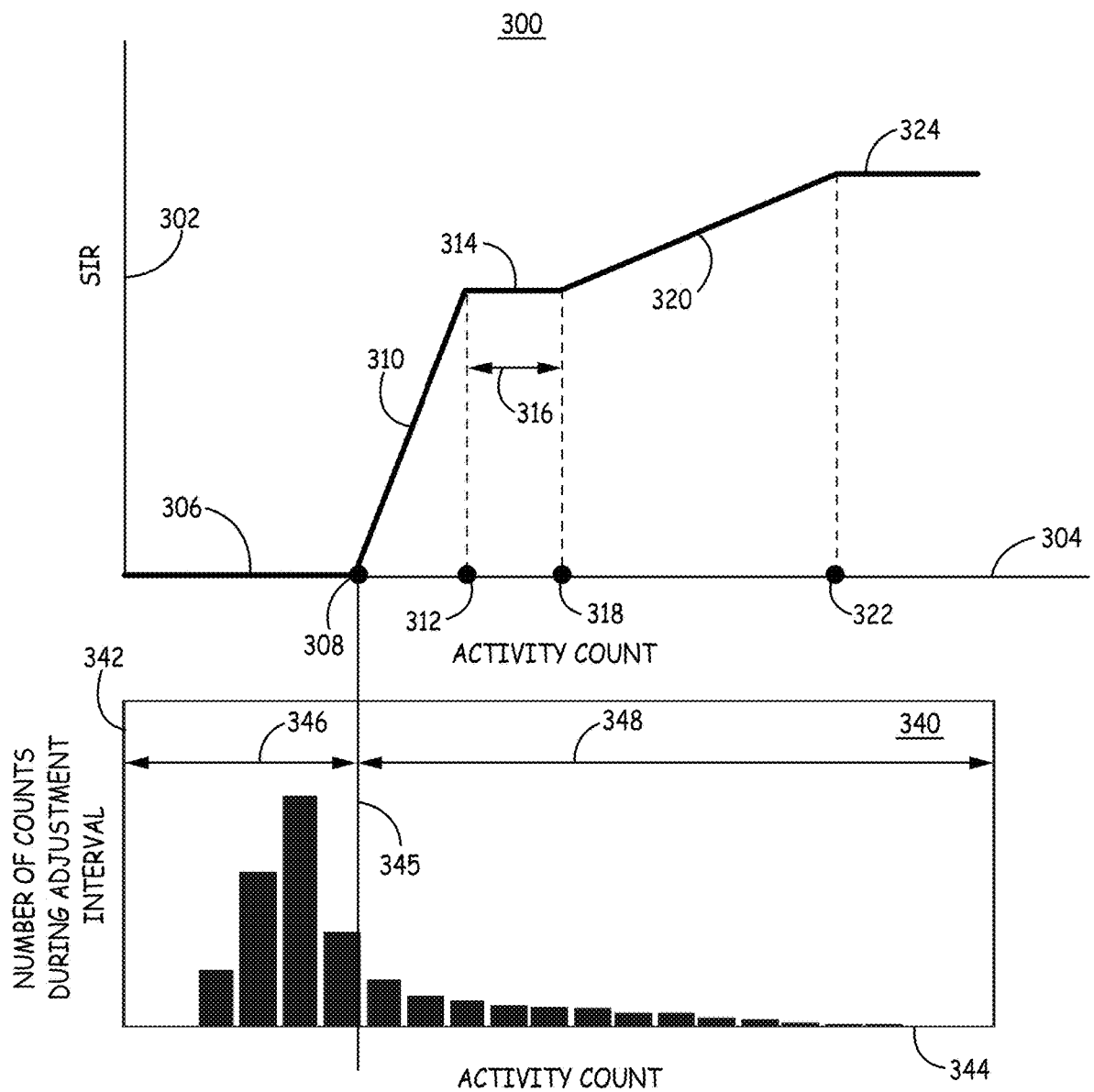
FIG. 4 is a plot of a sensor-indicated rate (SIR) transfer function determined by the pacemaker of FIG. 3 using activity counts determined from an accelerometer signal according to one example.

FIG. 4 is a plot 300 of a SIR transfer function determined by pacemaker 100 using activity counts determined from an activity sensor signal according to one illustrative example. In plot 300, SIR is plotted along the y-axis 302 as a function of activity count plotted along the x-axis 304. Control module 206 establishes a lower rate (LR) set point 308 based on an analysis of the activity counts determined over an interval of time as described below. The pacing rate is not adjusted above a lower rate 306, sometimes referred to as the "base pacing rate," as long as the activity count is at or below the LR set point 308.

As the activity count increases above the LR set point 308, the SIR may be determined according to an established profile between the SIR and the activity count. For example, an activities of daily living (ADL) lower set point 312 and ADL upper set point 318 may be established as the lower and upper boundaries of an activity count range that is expected to encompass the patient's activity level during normal daily activities and moderate activity, such as moving about the house, driving a car, light chores, etc. The SIR may be increased from the LR 306 to the ADL rate 314 according to a slope 310 between the LR set point 308 and the ADL lower set point 312. The SIR remains at the ADL rate 314 over the ADL range 316 between the ADL lower set point 312 and the ADL upper set point 318. An activity count above the upper ADL set point 318 will cause the pacemaker 100 to adjust the SIR according to a second slope 320 as a function of activity count up to a maximum upper rate set point 322. The SIR is set to the maximum upper pacing rate 324 for all activity counts greater than the maximum upper rate set point 322. Each of the lower ADL set point 312, upper ADL set point 318 and maximum upper rate set point 322 may be tailored to a patient's particular needs based on activity count history.

The LR set point 308 is established by the pacemaker 100 based on an analysis of activity counts sampled over an adjustment interval in some examples. The analysis of the activity counts over a predefined time interval may be thought of as an analysis of the activity count distribution over the predefined time interval as shown by the frequency plot 340 in FIG. 4. The number of activity counts occurring during a predefined time interval is shown along the y-axis 342 for each activity count value shown along the x-axis 344. In one example, the range of possible activity count values may be divided into predetermined activity count bins. The activity counts occurring in each bin are counted over the predefined time interval in one example. The activity count bin at the predetermined patient activity percentile 345 is identified and set as the LR set point 308.

For instance, an activity count may be determined every two seconds over a 24-hour adjustment interval. The activity count value at a predetermined percentile 345 of all activity count values accumulated over the adjustment interval is selected as the LR set point 308 in one example. The predetermined percentile 345 may be established as the percentage of time the patient is expected to require pacing at the LR 306, which can also be thought of as the percentage of time that the patient is expected to be at rest or non-active. The activity counts in a resting range 346 extending from an activity count of 0 up to percentile 345 represent activity counts that are expected to occur when the patient is at rest. The activity counts in this range 346 are highly likely to be due primarily to heart motion contributing to the activity sensor signal.

The activity count values in a non-resting activity range 348 extending from the percentile 345 to a maximum possible activity count represent activity counts that are expected to occur when the patient is active (not resting) and requires a pacing rate greater than the LR 306. In one example, the percentile 345 is selected as 85% such that the SIR is at the LR 306 approximately 85% of the time and will be increased above the LR 306 approximately 15% of the time.

As described below, the LR set point 308 may be increased or decreased to maintain the number of activity counts that are greater than the LR set point 308 within an acceptable variability range of an expected number of activity counts greater than the LR set point. Continuing with the example given above, if the patient activity percentile 345 is 85%, the activity counts in range 348 greater than the LR set point 308 are expected to be approximately 15% of all the activity counts determined over a monitoring interval. If more than 15% of the activity counts are greater than the LR set point 308, the LR set point 308 may be increased. If less than 15% of the activity counts are greater than the LR set point 308, the LR set point 308 may be decreased by control module 206.

Adjustments to the LR set point 308 may cause the slope 310 between the LR 306 and the ADL rate 314 to change. However, an adjustment to the LR set point 308 does not necessarily cause the lower ADL set point 312 to change. The lower ADL set point 312 may be changed if the slope 310 exceeds a slope limit, in which case the ADL set point 312 may be increased.

Figure 5:
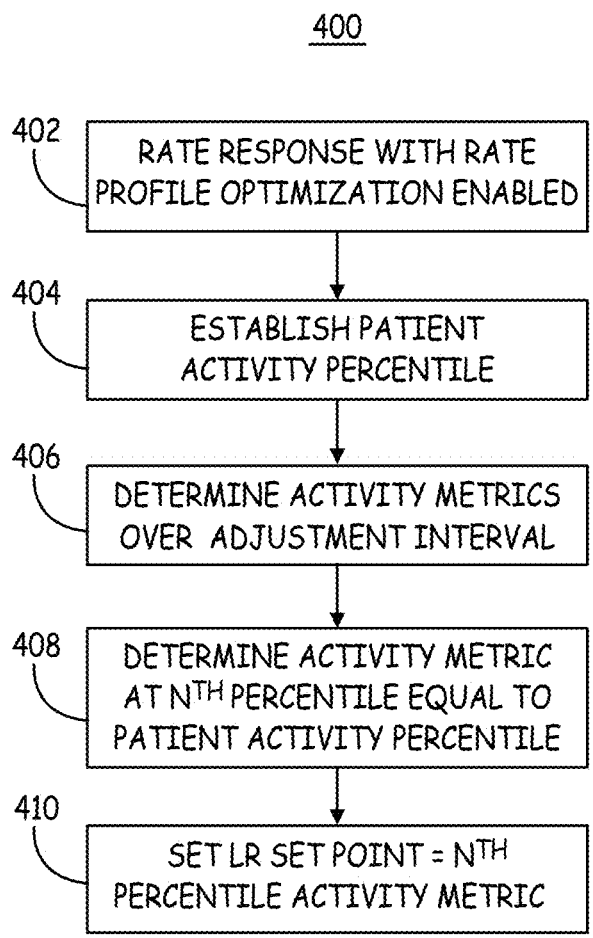
FIG. 5 is a flow chart of a method performed by the pacemaker of FIG. 3 for setting a lower rate (LR) set point used to control rate-responsive pacing according to a SIR.

FIG. 5 is a flow chart 400 of a method performed by pacemaker 100 for setting a LR set point 308 used to control rate-responsive pacing according to a SIR. At block 402, rate-responsive pacing is enabled. Rate-responsive pacing may be enabled upon pacemaker implantation or at any time after implantation. In some examples, in addition to enabling rate responsive pacing, rate profile optimization is enabled at block 402 in order for pacemaker 100 to customize the LR set point 308 for an individual patient. In other examples, rate profile optimization based on accumulating activity metrics in a given patient is performed automatically upon enabling rate responsive pacing.

At block 404, the patient activity percentile is established. The patient activity percentile is the percentage of time that the patient is expected to be inactive or at a resting level of activity. More specifically, the patient activity percentile is the percentage of time that the programmed lower rate is expected to adequately meet the patient's metabolic need. A resting level of activity may include any activity that does not require an increase in heart rate above a lower pacing rate for meeting an increased metabolic demand. Examples of resting activity include but are not limited to sleeping and lying quietly and may include sitting, e.g., while reading or watching TV.

In some examples, the patient activity percentile is a programmable value received from external device 20. The patient activity percentile may be established at block 404 based on a setting programmed by a user indicating a percentage of time the patient is expected to be resting and not requiring a pacing rate greater than the programmed lower rate. The percentage of time may be based on a 24-hour period, weekly period, monthly period or other time interval. In some examples, the programmer 20 may display numerical settings of 1 through 4, 1 through 5 or other numerical range where 1 indicates a relatively sedentary patient and 4 or 5 or other maximum range value indicates the highest level of activity that is expected for a patient.

To illustrate, a programmed value of "1" may be selected for a patient that is expected to be inactive at least 90% of every 24-hour period. This patient is expected to require pacing at a pacing rate above the programmed LR only about 10% of the time. A programmed value of "2" indicates that the patient is expected to be inactive at least 85% of the time and requires a pacing rate above the LR only approximately 15% of the time. A numerical value of "3" may be programmed for a patient that is expected to be inactive at least 80% of the time with pacing above the LR approximately 20% of the time, and a numerical value of "4" may be programmed for an active patient expected to be inactive only approximately 73% of the time with pacing above the LR approximately 27% of the time. A highest value of "5" may be programmed for a patient that is expected to be highly active requiring pacing at the LR approximately 65% of the time and above the LR approximately 35% of the time.

In other examples, different percentages may be used for pre-selected programmable patient activity percentiles than the examples given here. Additionally or alternatively, a user may have the option to manually select and program any desired percentile value that best fits the patient's daily or weekly physical activity profile.

At block 406, an activity metric is sampled over an LR set point adjustment interval. The control module 206 determines the activity metric value that is at the patient activity percentile at block 408 at the expiration of the adjustment interval. The LR set point is set to the activity metric value at the patient activity percentile at block 410.

In some examples, the activity metrics determined at block 406 are activity counts determined every 2 seconds over a 24-hour adjustment interval. At the end of the adjustment interval, the activity counts accumulated at every 2-second interval are sorted smallest to largest. The activity count that is the Nth percentile of all activity count values stored over the adjustment interval is determined at block 408, where the Nth percentile equals the established patient activity percentile. The Nth percentile activity count represents the lower boundary of the non-resting range of activity counts for the patient based on the established patient activity percentile. Stated differently, the Nth percentile activity count represents the upper boundary of the resting range of activity counts that may occur due to heart motion while the patient is at rest or in a non-active state.

The Nth percentile activity count is set as LR set point at block 410. The activity counts equal to or less than the Nth percentile represent activity counts that will produce a SIR equal to the programmed LR. The activity counts above the Nth percentile represent a true increase in patient activity above rest and are therefore activity counts that will produce a SIR greater than the programmed LR. The activity counts above the Nth percentile represent the (100−N) % of the time the patient is expected to be active and require a pacing rate greater than the LR where N is the established patient activity percentile. In this way, non-zero activity count values that are due primarily to heart motion when the patient is at rest are filtered from the activity count values that are used to adjust the SIR above the LR.

Figure 6:
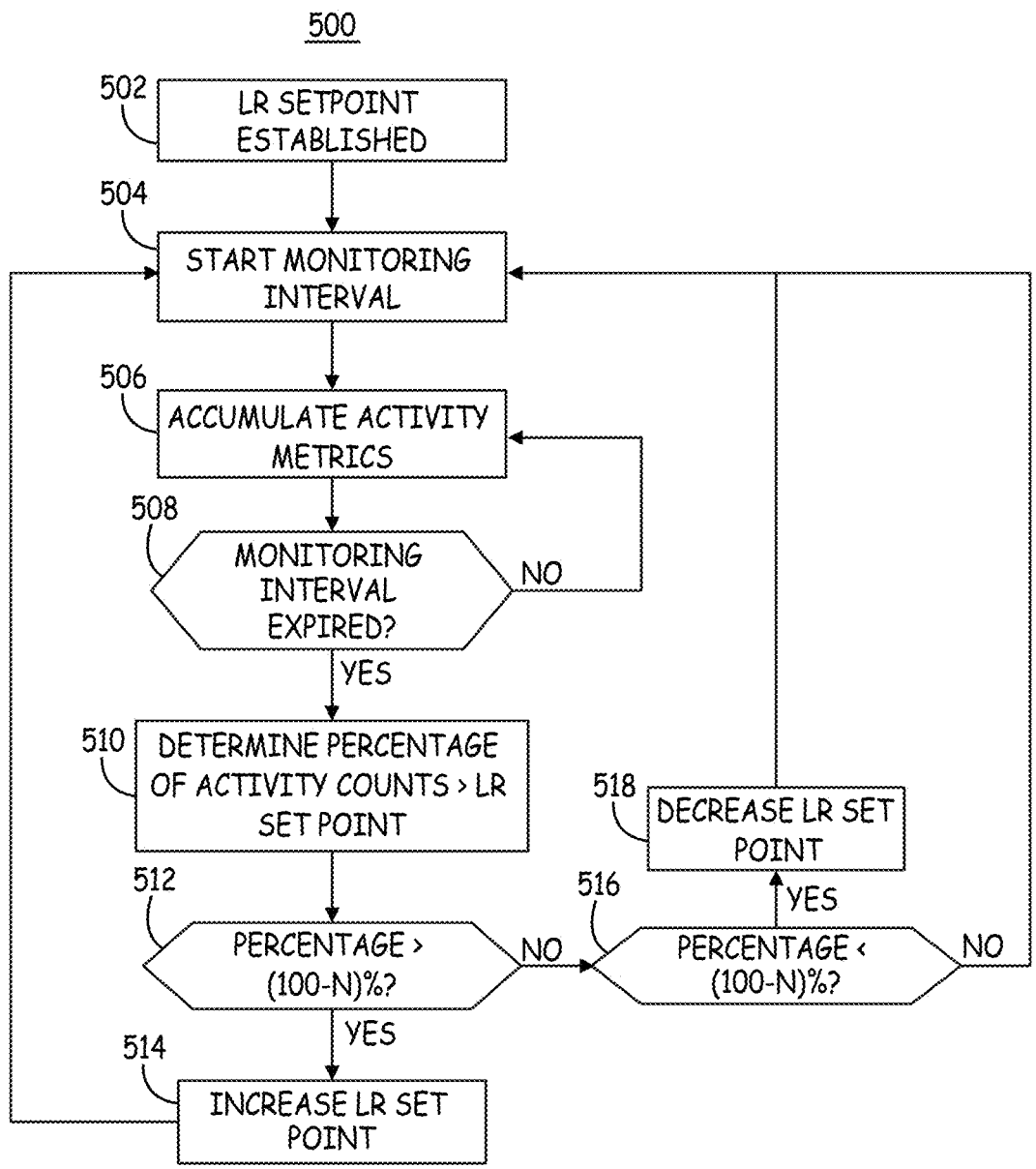
FIG. 6 is a flow chart of a method for automatically adjusting the LR set point according to one example.

FIG. 6 is a flow chart 500 of a method for automatically adjusting an established LR set point according to one example. At block 502, the LR set point is established by the control module 206 according to the method shown in FIG. 5. In another example, the LR set point may be set to a nominally programmed value initially. At block 504, a monitoring interval is started, which may be a 24-hour period or other desired time period. The monitoring interval is a time period after the adjustment interval that is used to establish the LR set point upon enabling rate responsive pacing. At block 506, activity metrics are accumulated over the monitoring interval. The activity metrics may be 2-second activity counts accumulated over a 24-hour monitoring interval as described previously.

If the monitoring interval expires, as determined at block 508, the control module 206 determines the percentage of activity metrics accumulated during the monitoring interval that are greater than the established LR set point at block 510. The percentage of activity metrics that is greater than the LR set point is compared to the percentage of activity metrics expected to be greater than the LR set point at blocks 512 and 516. The expected percentage is (100−N) % where N is the patient activity percentile used to establish the LR set point in the process shown by the flow chart 400 of FIG. 5.

If the percentage of activity metrics that are greater than the LR set point is greater than the expected percentage, as determined at block 512, the LR set point is increased at block 514. If the percentage of activity metrics that are greater than the LR set point is less than the expected percentage as determined at block 516, the LR set point is decreased at block 518. Otherwise, the LR set point remains unchanged, and the process returns to block 504 to start the next monitoring interval.

By setting the LR set point at a predetermined percentile of all of the activity metrics determined over a monitoring interval, heart motion is effectively filtered from the activity counts that cause the SIR to increase above the LR set point. If the number of activity counts during a monitoring interval is greater than the expected number of activity counts based on the patient's activity percentile ("yes" branch of block 512), some of the higher activity counts may be due to heart motion rather than a real increase in patient activity. The contribution of heart motion to the activity sensor signal may change over time, e.g., as the position of pacemaker 100 changes relative to the heart. As such, the LR set point is adjusted upward at block 514 to promote pacing above the SIR at the expected (100−N) % of the time and pacing at the LR N % of the time, equal to the patient activity percentile.

If the activity counts trend lower ("yes" branch of block 516), heart motion may be contributing less to the activity sensor signal. In this case, the LR set point is reduced at block 518 to maintain pacing above the SIR the expected (100−N) % of the time and pacing at the LR N % of the time equal to the patient activity percentile.

Heart motion contribution to the activity sensor signal may vary over time. Changes in patient posture or rotation of the intracardiac pacemaker 100 relative to the heart may alter the axis of an accelerometer activity sensor relative to heart motion. Adjustments to the LR set point allow the heart motion contribution to the activity sensor to be filtered from the activity metrics such that the SIR is increased above the LR appropriately when a true increase in metabolic demand is likely.

The amount that the LR set point is increased or decreased at blocks 514 and 518 respectively may vary between embodiments. In one example, the LR set point is adjusted by a maximum of one activity metric unit, for example one count. In this example, the LR set point is adjusted by +1, −1 or 0 after each monitoring interval. By limiting the increment and decrement size, the LR set point is not changed drastically in response to one monitoring period in which the patient is unusually inactive or one monitoring period in which the patient is unusually active. A monitoring interval during which the patient is highly active compared to the expected patient activity percentile will have the effect of increasing the LR set point by one count. A monitoring interval during which the patient is highly sedentary, e.g., due to illness, may have the effect of decreasing the LR set point by one count. When the patient resumes normal activities, the LR set point will return to the desired percentile to promote pacing at the LR according to the previously established patient activity percentile. If the percentage of time that the patient is actually active increases or decreases, e.g., due to a change in health, the patient activity percentile may be re-established accordingly to allow the LR set point to be adjusted to a higher or lower percentile of activity counts as needed. For example, as a patient's lifestyle changes, a clinician or other user may reprogram the patient activity percentile.

In other examples, the LR set point 308 may be adjusted by a scaled increment or decrement based on the difference between the percentage of activity counts greater than the LR set point and the expected percentage. In some cases, the LR set point 308 may be adjusted by more than one activity metric unit or by a fraction of an activity metric unit at the expiration of a monitoring interval based on the difference.

In some examples, the percentage of activity metrics that are greater than the LR set point 308 is compared to a target range of the expected (100−N) %. If the actual number of activity metrics greater than the LR set point 308 falls within the target range, no change to the LR set point is made. In some instances, the target range is defined by a maximum number of activity counts that are expected to be greater than the LR set point 308 during each monitoring interval and a minimum number of activity counts that are expected to be greater than the LR set point. The maximum and minimum boundaries of the target range may be stored in pacemaker memory 210 and may be user-programmable values, e.g., programmed as a percentage of activity metrics accumulated over a monitoring interval. If the programmed maximum number of activity counts expected to be greater than the LR set point is exceeded, the LR set point is increased. If the minimum number of activity counts that are expected to be greater than the LR set point is not reached during the monitoring interval, the LR set point is decreased.

It is recognized that numerous schemes may be conceived for adjusting the LR set point in response to detecting a difference between the actual number of activity metrics greater than the LR set point and an expected number of activity metrics greater than the LR set point during a monitoring interval, where the expected number may be based on a programmed patient activity percentile. Generally, the LR set point adjustments may be limited to a maximum adjustment size, e.g., one activity count, to avoid large fluctuations in the LR set point due to one relatively sedentary monitoring interval or one extremely active monitoring interval that does not typify the patient's normal daily routine.

Figure 7:
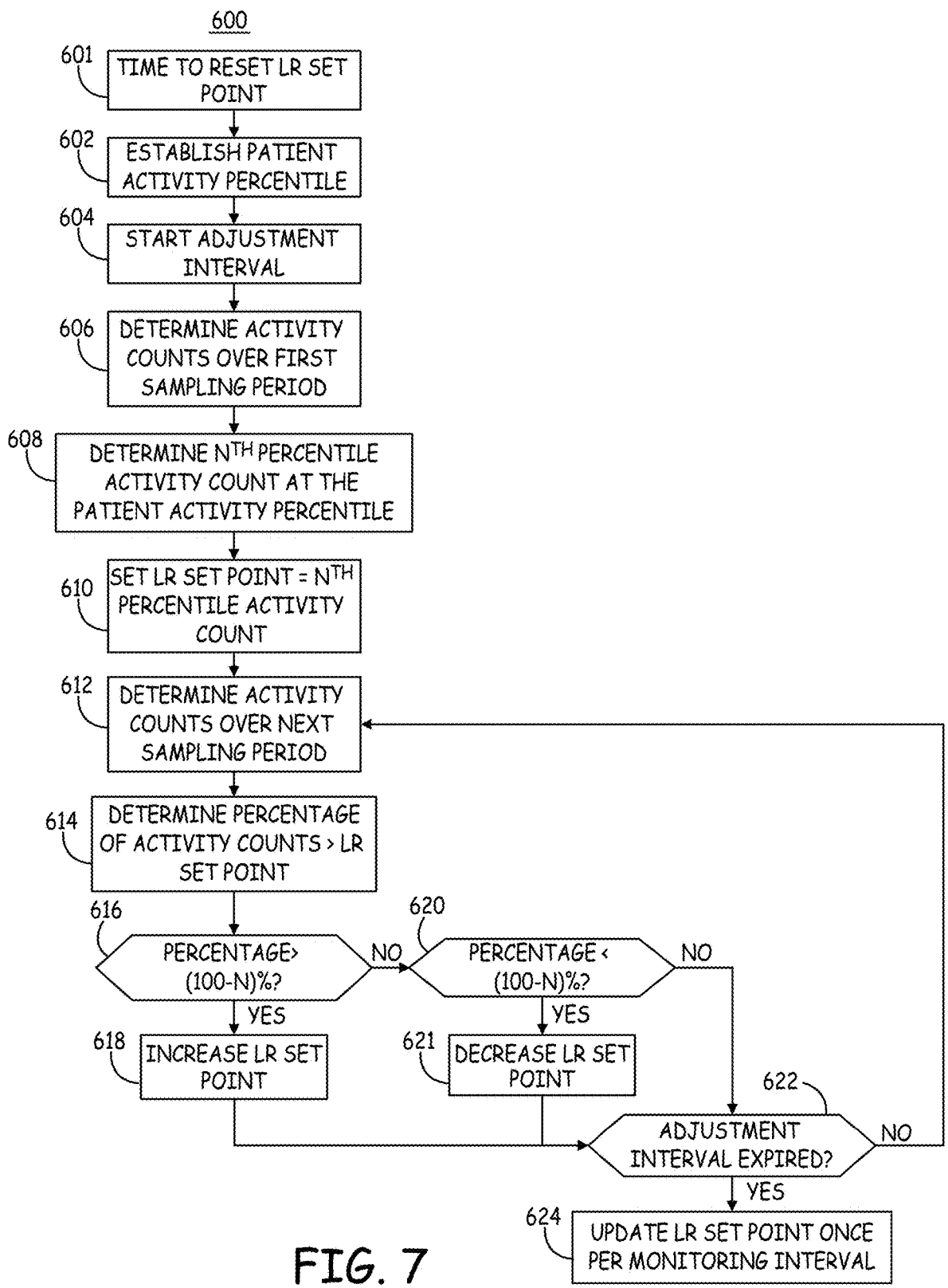
FIG. 7 is a flow chart of a method for establishing the LR set point based on a programmed patient activity percentile and updating the LR set point over time according to one example.

FIG. 7 is a flow chart 600 of a method for establishing the LR set point based on a programmed patient activity percentile and updating the LR set point over time according to one example. At block 601, the pacemaker 100 may determine that the LR set point needs to be established or re-established. The LR set point may initially be established upon pacemaker implantation, but may be re-established after reprogramming operating parameters of the pacemaker, such as enabling rate responsive pacing, enabling pacing rate profile optimization, programming the patient activity percentile to a new value after a health-related, lifestyle or prescription change in the patient, or other programming change that may impact the rate-responsive pacing performance desired from pacemaker 100. The patient activity percentile is established at block 602, for example as a default nominal value or a user-programmed value stored in pacemaker memory 210.

At block 604, an adjustment interval is started during which the LR set point will be rapidly adjusted from an initial value based on activity metrics accumulated during the adjustment interval. In some examples, the initial value of the LR set point is a default or programmed value that may be set conservatively to avoid an increase in pacing rate due to the influence of heart motion on the activity sensor signal. This strategy may be used, for example, after pacemaker implantation since the patient is expected to be relatively inactive during recovery and not require pacing above the LR. The LR set point will be adjusted during the adjustment interval from the initially conservative value to an appropriate value for the patient based on the activity counts accumulated from the patient during the adjustment interval and the programmed patient activity percentile.

In other examples, the initial value of the LR set point is a previously established LR set point that may have been automatically adjusted under different programmed parameters after one or more monitoring intervals. This previously established LR set point may be the starting point of the process shown in flow chart 600 when the pacemaker 100 determines that it is time to reset the LR set point.

During the adjustment interval started at block 604, the LR set point will be adjusted according to activity metrics determined during the adjustment interval. In one example, the adjustment interval is 24 hours, but in alternative embodiments the adjustment interval may be shorter, e.g., eight hours, twelve hours, or longer, for example two to seven days.

At block 606, a series of activity metrics is determined from the activity sensor signal over a first sampling period. In the example of flow chart 600, the activity metric is an activity count that is stored in memory 210 at the end of each 2-second (or other predetermined) activity count interval. The adjustment interval started at block 604 is divided into multiple sampling periods. At the expiration of the first sampling period, the initial LR set point is set based on the 2-second activity counts accumulated during the sampling period as will be described below.

The sampling period may be one hour, 1.5 hours, 2 hours, 4 hours, or other portion of the adjustment interval. By adjusting the LR set point at the expiration of each relatively short sampling period over an adjustment interval, the LR set point can be rapidly adjusted from its initial value toward a new LR set point. In one example, the adjustment interval is a 24-hour period during which the LR set point is adjusted after every 90 minute sampling period based on activity counts accumulated at n-second intervals during the sampling period. As indicated above, the initial value of the LR set point at the start of the adjustment interval may be a default, conservative value or a previously established value that may no longer be relevant under new circumstances, e.g., newly programmed parameters. The initial value is rapidly adjusted toward a new LR set point that is most appropriate for the patient based on their daily routines and/or newly programmed parameters.

Alternatively, an initial value of the LR set point may be established during the first sampling period. In flow chart 600, a series of activity counts is determined over the first sampling period at block 606. Upon expiration of the first sampling period, the activity count that is at the established patient activity percentile during the sampling period is determined at block 608. The LR set point is set at block 610 based on the activity count determined to be at the Nth percentile equal to the programmed patient activity percentile at the expiration of the first sampling period. In other examples, the initial LR set point is a programmed value and is adjusted from the initial value at the expiration of the first sampling period based on a comparison of the number of activity counts during the first sampling period that are greater than the initially programmed LR set point to an expected number of activity counts equal to N %.

The LR set point may be adjusted from an initial value based on patient activity metrics within one sampling period after determining a need to establish a LR set point. For example, upon pacemaker implantation, the LR set point is adjusted within one sampling period after implantation based on actual activity metric data. By starting with a relatively conservative LR set point upon implantation, the LR set point may start high during recovery from the implantation procedure and will be adjusted frequently, i.e., after each sampling period, over the adjustment interval as the patient returns to normal activity.

The activity count continues to be determined at n-second intervals during the next sampling period at block 612. Upon expiration of the next sampling period, the percentage of activity counts during the sampling period that is greater than the LR set point is determined at block 614. If the percentage of activity counts greater than the LR set point during the sampling period is greater than the expected percentage (100–N) % ("yes" branch of decision block 616), the LR set point is increased at block 618. If the percentage of activity counts greater than the LR set point during the next sampling period is less than the patient activity percentile ("yes" branch of block 620), the LR set point is decreased at block 621.

As described above, the LR set point may be increased or decreased at blocks 618 or 621, respectively, by on one count, a fraction of one count, or more than one count based on a predefined LR set point increment or decrement. The LR set point increment or decrement may be a scaled increment or decrement based on the difference between the percentage determined at block 614 and the expected percentage.

It is recognized that when the sampling period has a fixed duration, a known number of n-second intervals, i.e., a known number of activity counts, will be determined during each sampling interval. As such, the determination made at block 614 may be a determination of the number of activity counts that are greater than the LR set point rather than a percentage, and that number of activity counts may be compared directly to an expected number of activity counts at block 616 rather than a comparison of percentages. For example, 2,700 2-second activity counts may be accumulated over a 90 minute sampling period. If the patient activity percentile is programmed to 85%, 15% of the 2,700 activity counts, or 405 activity counts, are expected to be greater than the LR set point. If the actual number of activity counts are greater than or less than the expected 405 activity counts, the LR set point may be adjusted.

If the percentage of activity counts greater than the LR set point during the next sampling interval is not greater than or less than the patient activity percentile ("no" branch of block 620), the process proceeds to block 612 to accumulate activity counts over the next sampling period and adjust the LR set point if needed at the expiration of the next sampling period. This process of looping back to block 612 continues until the adjustment interval expires (as determined at block 622). Once the adjustment interval expires, the LR set point has been established for the given patient by way of multiple adjustments (at the expiration of each sampling period) over the adjustment interval.

In another example, instead of adjusting the actual LR set point at the expiration of each sampling period, an updated LR set point value may be stored in memory at the expiration of each sampling period without adjusting the actual LR set point. The stored, updated LR set point value may be adjusted at the expiration of each sampling interval without changing the initial LR set point value existing at the start of the adjustment interval (or, in the alternative, established after one sampling period). The actual LR set point may be adjusted to the stored, updated LR set point value upon expiration of the adjustment interval at block 622. In this way, the actual LR set point is adjusted a single time at the end of the adjustment interval, but may be adjusted by a single large increment or decrement as needed to match the stored, updated LR set point value that has been adjusted as needed after each sampling period.

After the adjustment interval, the control module 206 may update the LR set point as needed at the expiration of regular monitoring intervals as indicated at block 624. The LR set point may be updated at block 624 at the expiration of each monitoring interval according to the method described above in conjunction with FIG. 6.

The monitoring interval may be 24 hours or another interval of time that is longer than the sampling period used to rapidly adjust the LR set point during the adjustment interval. The monitoring interval may be the same duration as the adjustment interval, but may be longer or shorter in some examples. In one example, the LR set point is adjusted every 90 minutes during a 24 hour adjustment interval and then updated only once every 24 hours at the expiration of every 24-hour monitoring interval thereafter. In another example, the LR set point is adjusted after every 90 minute sampling period during a 48-hour adjustment interval and then updated once after every 24-hour monitoring interval thereafter. The sampling period, adjustment interval and monitoring interval may vary between embodiments and may be predefined or programmable time periods based on patient need.

Figure 8:
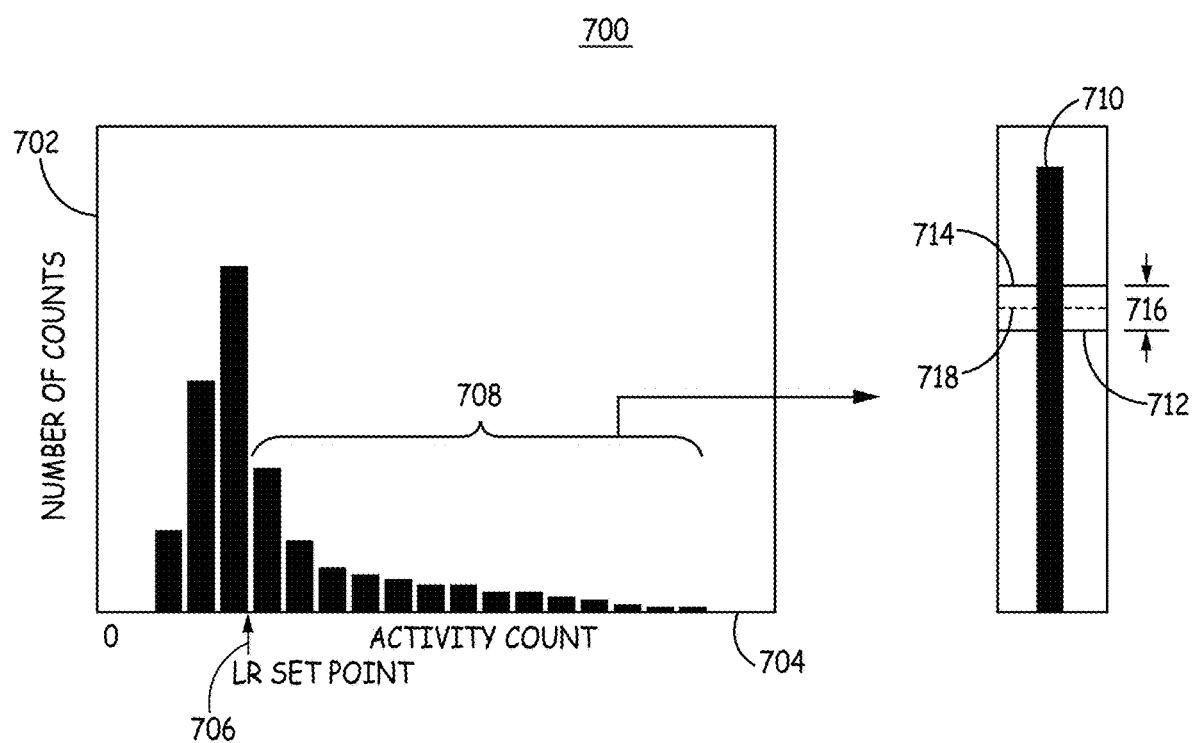
FIG. 8 is a frequency plot of activity counts accumulated over a period of time and illustrating one method for adjusting the LR set point.

FIG. 8 is a frequency plot 700 of activity counts accumulated over a period of time, which may be a sampling period during an adjustment interval or over a monitoring interval following an adjustment interval. Activity count is shown along the x-axis 704, and the frequency or number of activity counts occurring during the time period at each activity count value is plotted along y-axis 702. A LR set point 706 has been established. At the expiration of each sampling period within an adjustment interval or at the expiration of the monitoring interval, the activity counts 708 that are greater than the LR set point 706 are counted to obtain a total number of counts 710 greater than the LR set point 706. The total number of counts 710 may be determined as a count of the n-second intervals during the time period that ended with an activity count greater than the LR set point 706. Alternatively, the total number of activity counts 710 may be determined as a percentage of all activity counts (for all counting time intervals) during the time period.

The total number of counts 710 that exceed the LR set point 706 is compared to a maximum number of activity counts 714 expected to exceed the LR set point 706 during the time period and to a minimum number of activity counts 712 expected to exceed the LR set point 706 during the time period. An acceptable activity count variation range 716 is defined by the maximum activity count number 714 and the minimum activity count number 712. A targeted number of activity counts 718 that are greater than the LR set point 706 is equal to (100−N) % of the total activity counts accumulated over the time period, where N is the established patient activity percentile. The variation range 716 may be defined as a fixed increment greater than and less than the target number of activity accounts 718 or as a predetermined percentage of the total accumulated activity counts greater than and less than the target number of counts 718, e.g., +5%, +10% or another percentage of the total accumulated activity counts during the time interval.

The LR set point 706 is adjusted up or down to move the total number of activity counts 710 that are greater than the LR set point 706 toward the target number of activity counts 718, which is to 100% minus the patient activity percentile. If the total number of counts 710 that are greater than the LR set point 706 falls within range 716, no adjustment to the LR set point is made at the expiration of the time period.

The maximum activity count 714 and the minimum activity count 712 may be defined differently if the total number activity counts 710 has been accumulated over a relatively shorter sampling period during an adjustment interval than if the total number of activity counts 710 has been accumulated during a relatively longer monitoring interval (after the adjustment interval). For example, a relatively narrower range 716 may be defined for a sampling period and a relatively wider range may be defined for a longer, monitoring period.

In the example shown, the total number of activity counts 710 that are greater than the LR set point 706 exceeds the maximum number of activity counts 714 indicating that the LR set point 706 may be set too low. The control module 206 adjusts the LR set point 706 by increasing it according to a predetermined increment, which may be a fixed value or scaled value based on the total number of activity counts 710 that are greater than the LR set point 706 as described above.

Figure 9:
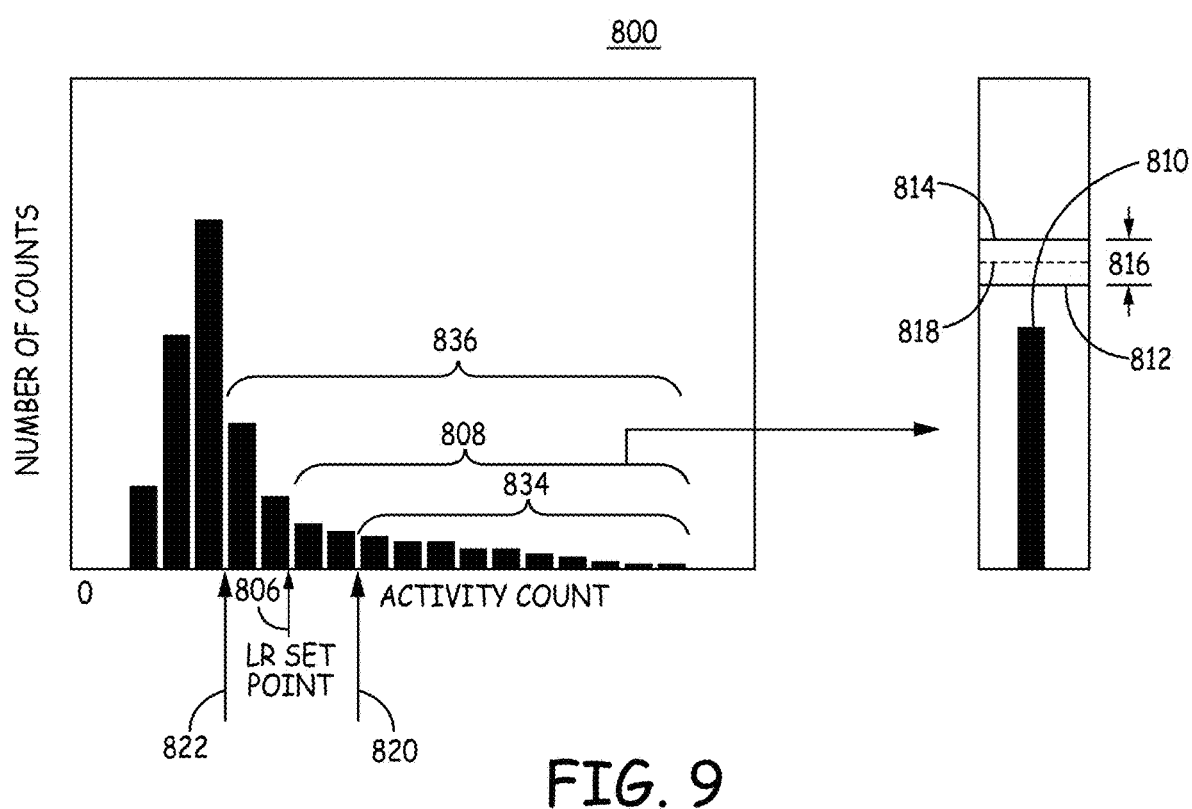
FIG. 9 is a frequency plot of activity counts accumulated over a period of time and illustrating another method for adjusting the LR set point.

FIG. 9 is a frequency plot 800 of activity counts accumulated over a period of time, which may be a sampling period during an adjustment interval or over a monitoring interval following an adjustment interval. In this example, the total number of activity counts 810 that exceed the LR set point 806 (all activity counts 808 above LR set point 806) is less than a minimum number of activity counts 812 expected to be greater than the LR set point 806. Since the total number of activity counts 810 that exceed the LR set point 806 falls outside the acceptable activity count variation range 816 of a target number of activity counts 818, defined by the maximum number of activity counts 814 and the minimum number activity counts 812 expected to be greater than the LR set point 806, the LR set point 806 is adjusted or updated at the expiration of the time period. In this case, the LR set point 806 is decreased according to a fixed or scaled decrement based on total number of activity counts 810 that are greater than the LR set point 806 in order to move the total number of activity counts 810 that are greater than the LR set point 806 during the next time interval toward the target number of activity counts 818.

In addition to determining the total number of activity counts greater than the LR set point 806, control module 206 may be configured to determine the number of activity counts that exceed a second higher threshold 820 greater than the LR set point 806 and/or a third threshold 822 less than the LR set point 806. In some examples, control module 206 includes a counter that counts the total number of activity counts 810 that exceed the LR set point 806. In addition to that counter, control module 206 may include a second counter that determines the total number of activity counts 834 that are above a second higher threshold 820 and a third counter that determines the total number of activity counts 836 that are greater than the third, lower threshold 822.

In one example, the second higher threshold 820 is set to the LR set point 806 plus a fixed increment, e.g., the LR set point 806 plus two activity count units. The third lower threshold 822 may be set at the LR set point 806 less a fixed decrement, e.g., the LR set point 806 minus three activity count units. In another example, the higher threshold 820 is set to a percentile greater than the percentile at the LR set point 806, and the lower threshold 822 is set to a percentile less than the percentile at which LR set point 806 is set. For example, if the patient activity percentile is 85%, the LR set point 806 is set at the 85th percentile of previously accumulated activity counts (e.g., based on the activity counts during a previous sampling period or previous monitoring interval). The higher threshold 820 may be set to 90th percentile of the previously accumulated activity counts, and the lower threshold 822 may be set to the 80th percentile of the previously accumulated activity counts.

As described previously herein, the LR set point 806 may be adjusted by 0, +1, or −1 at the end to each sampling period during an adjustment interval, based on the comparison of the total number of activity counts 810 to the acceptable variability range 816. In other instances, the LR set point 806 may be adjusted by an increment greater than +1 if the total number of activity counts 834 that are greater than the higher threshold 820 is greater than an expected number of activity counts. Likewise, the LR set point 806 may be adjusted by a larger decrement than −1 if the total number of activity counts 836 that are greater than the lower threshold 822 is less than an expected number of activity counts.

To illustrate, if the patient activity percentile is set to 85%, pacing above the LR is expected approximately 15% of the time. The total number of activity counts 808 greater than the LR set point 806 is expected to be approximately 15% of the total number of activity counts accumulated during the sampling period. The control module 206 may be configured to determine the total number of activity counts 834 that are greater than a higher threshold 820, which may be set to the activity count that is 5% higher than the patient activity percentile, e.g., the 90th percentile, of previously accumulated activity counts. The total number of activity counts 834 greater than the higher threshold 820 may be compared to an expected 10% of the total number of activity counts accumulated during the sampling period. If the total number of activity counts 834 that are greater than the higher threshold 820 represent more than the expected 10% of the total number of activity counts, the LR set point 806 may be increased by more than +1. In some examples, the LR set point is increased by +2 or +3 instead of +1.

The lower threshold 822 may be set to an activity count at a percentile less than the percentile that the LR set point 806 is set to, e.g., 5% less or at the 80th percentile in the illustrative example given above. When set at the 80th percentile, approximately 20% of all of all the activity counts accumulated during the current sampling period are expected to be greater than the lower threshold 822. If the total number of activity counts 836 greater than the lower threshold 822 is less than the expected 20% of the total accumulated activity counts during the sampling period, the LR set point 806 may be adjusted by a decrement greater than −1, e.g., −2 or −3, at the expiration of the sampling period.

In this way, the amount that the LR set point 806 is increased or decreased at the end of a sampling period may be based on an analysis of the frequency of activity counts above different activity count thresholds 806, 820 and 822. Adjustments to the LR set point 806 made in this way may move the LR set point 806 to the activity count at the patient activity percentile relatively faster. In some embodiments, as described above, a stored LR set point value may be adjusted according to an analysis of activity counts that includes determining total numbers of activity counts greater than multiple activity count thresholds without adjusting the actual LR set point until the adjustment interval has expired. The LR set point 806 used to set the pacing rate during the adjustment interval may remain fixed at an initial LR set point, and the initial LR set point 806 is adjusted in one step to a stored, updated LR set point value that has been updated after every sampling period.

Figure 10:
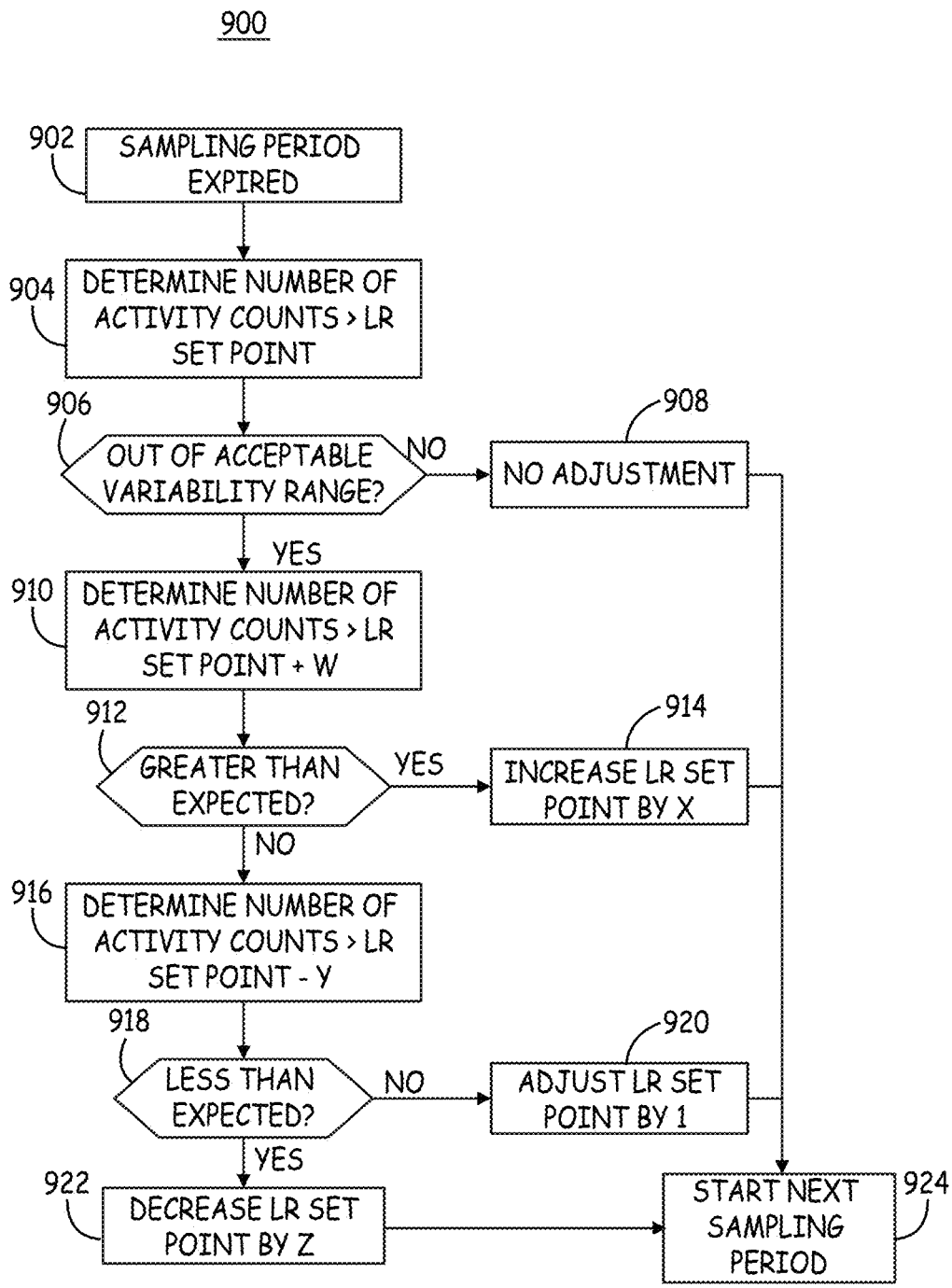
FIG. 10 is a flow chart of a method for adjusting the LR set point according to another example.

FIG. 10 is a flow chart 900 of a method for adjusting the LR set point according to the methods described in conjunction with the frequency plot of FIG. 8. As described above, the control module 206 may be configured to adjust the LR set point at the expiration of each sampling period during an adjustment interval. The adjustment to the LR set point during the adjustment interval may be of different sizes, i.e., different increments or decrements as needed, based on comparisons of the frequency of activity counts that occur above different thresholds to expected frequencies for each of the respective thresholds.

Upon expiration of a sampling period at block 902, the control module determines the total number of activity counts during the sampling period that are greater than the LR set point at block 904. At block 906, the control module 206 compares the total number of activity counts greater than the LR set point to the acceptable variability range of the targeted, expected number of activity counts greater than the LR set point. If the total number of activity counts greater than the LR set point is within the variability range at block 906, the LR set point is not adjusted at block 908. The next sampling period is started at block 924.

If the total number of activity counts greater than the LR set point is outside the variability range at block 906, the control module 206 determines the total number of activity counts greater than a higher activity count threshold, e.g., the LR set point plus W, where W may be 1, 2, 3 or other number of activity count units or a percentage of the LR set point. The number of activity counts greater than the LR set point+W is compared to the number of activity counts that are expected to be greater than the LR set point+W at block 912.

If the total number of activity counts greater than the LR set point+W is greater than the expected number, the LR set point is increased by an increment X that is greater than +1 activity count unit at block 914. For example, the LR set point may be increased by +3 in response to the total number of activity counts greater than the LR set point+W being greater than expected. If the total number of activity counts greater than the LR set point+W is not greater than expected, the control module determines the number of activity counts that are greater than the LR set point−Y at block 916.

If the number of activity counts that are greater than the lower threshold, LR set point−Y, is less than expected, as determined at block 918, the LR set point is decreased by a decrement Z that is a larger decrement than −1 activity count units at block 922. For example, the LR set point may be decreased by −2 at block 918 if the total number of activity counts greater than the LR set point−Y is less than expected.

If the number of activity counts is not less than expected at block 918 (and not greater than expected at block 912), the LR set point is adjusted by +1 at block 920. In this case, the number of activity counts greater than the LR set point is outside the acceptable variability range ("yes" branch of block 906) but not greater than the higher threshold ("no" branch of block 912) and not less than the lower threshold ("no" branch of block 918). Accordingly, an adjustment is indicated but a relatively smaller increment or decrement to the LR set point is made at block 920 than the increment made at block 914 or the decrement made at block 922.

The adjustment made at block 920 is an increase of +1 (or other predetermined increment) to the LR set point if the number of activity counts greater than the LR set point is greater than the upper boundary of the acceptable variability range and the number of activity counts greater than LR set point+W is not greater than expected. The adjustment made at block 920 is a decrease of −1 (or other predetermined decrement) to the LR set point if the number of activity counts greater than the LR set point is less than the lower boundary of the acceptable variability range and the number of activity counts greater than the LR set point−Y is not less than expected. The LR set point is adjusted at one of blocks 914, 920 or 922, or not adjusted at block 908, based on an analysis of the activity counts accumulated during the expired sampling period that are greater than the LR set point and one or more additional thresholds. The next sampling period is started at block 924.

The control module 206 continues this process until the adjustment interval expires. In one example, the process shown by FIG. 10 is executed only during the adjustment interval. Adjustments made at the expiration of a monitoring interval following the adjustment interval may be limited to single step adjustments, e.g., −1, 0, or +1, based on a comparison to the acceptable variability range of the target number of activity counts greater than the LR set point. In other examples, larger adjustments to the LR set point may be made at the expiration of the monitoring interval based on comparisons to higher and lower threshold as described in conjunction with FIG. 10.

It is recognized that the techniques described in conjunction with the flow charts and drawings presented herein may be combined in different combinations than shown and described here. For example, other combinations of activity metric analysis and LR set point adjustments other than the specific examples and combinations described herein may be used for defining a SIR transfer function that optimizes the rate response behavior of the pacemaker 100 for an individual patient.

Thus, various embodiments of a medical device and method have been described for establishing a lower rate set point for use in controlling rate responsive pacing. However, one of ordinary skill in the art will appreciate that various modifications may be made to the described embodiments without departing from the scope of the following claims.

What is claimed is:

1. An implantable cardiac device comprising:
    a housing configured to be implanted within a heart of a patient;
    an accelerometer positioned within the housing, the accelerometer configured to generate an accelerometer signal; and
    a control circuit configured to:
        determine, based on application of one or more thresholds to the accelerometer signal, a plurality of activity metrics based on a portion of the accelerometer signal over a first time period, wherein each activity metric of the plurality of activity metrics indicates an amount of motion of the accelerometer during a respective window of time within the first time period;
        identify a first set of activity metrics including each activity metric of the plurality of activity metrics that is less than a threshold activity metric, wherein the first set of activity metrics correspond to heart motion when the patient is at rest;
        identify a second set of activity metrics including each activity metric of the plurality of activity metrics that is greater than the threshold activity metric;
        filter, from the plurality of activity metrics, the first set of activity metrics corresponding to heart motion when the patient is at rest so that the filtered plurality of activity metrics includes the second set of activity metrics without including the first set of activity metrics, wherein the filtered plurality of activity metrics corresponds to the portion of the accelerometer signal over the first time period;
        determine, based on the filtered plurality of activity metrics, a pacing rate; and
        cause a pulse generator to generate pacing pulses over a second time period at the pacing rate, wherein the second time period occurs after the first time period.

2. The implantable cardiac device of claim 1, wherein the control circuit is configured to determine the plurality of activity metrics over the first time period by determining a plurality of activity counts over the first time period.

3. The implantable cardiac device of claim 2, wherein the control circuit is configured to filter, from the plurality of activity metrics, the first set of activity metrics by filtering a non-zero number of activity counts from the plurality of activity counts, the non-zero number of activity counts corresponding to the heart motion when the patient is at rest.

4. The implantable cardiac device of claim 1,
    wherein the control circuit is configured to identify the first set of activity metrics including each of the plurality of activity metrics that is less than the threshold such that the first set of activity metrics represents a first percentile of the plurality of activity metrics, and
    wherein the control circuit is configured to identify the second set of activity metrics including each of the plurality of activity metrics that is greater than the threshold such that the second set of activity metrics represents a second percentile of the plurality of activity metrics.

5. The implantable cardiac device of claim 4, wherein the first percentile is 85%, and wherein the second percentile is 15%.

6. The implantable cardiac device of claim 1, wherein the control circuit is configured to determine the pacing rate by determining a lowest pacing rate for pacing the heart.

7. The implantable cardiac device of claim 1, wherein the first time period comprises a pacing rate adjustment interval.

8. The implantable cardiac device of claim 7, wherein the pacing rate adjustment interval comprises a 24-hour time period.

9. A method comprising:
determining, by a control circuit of an implantable cardiac device based on application of one or more thresholds to an accelerometer signal, a plurality of activity metrics based on a portion of the accelerometer signal over a first time period, wherein the implantable cardiac device comprises a housing configured to be implanted within a heart of a patient, and wherein the implantable cardiac device comprises an accelerometer positioned within the housing, the accelerometer configured to generate the accelerometer signal, wherein each of the plurality of activity metrics indicates an amount of motion of the accelerometer during a respective window of time within the first time period;
identifying, by the control circuit, a first set of activity metrics including each activity metric of the plurality of activity metrics that is less than a threshold activity metric, wherein the first set of activity metrics correspond to heart motion when the patient is at rest;
identifying, by the control circuit a second set of activity metrics including each activity metric of the plurality of activity metrics that is greater than the threshold activity metric;
filtering, by the control circuit from the plurality of activity metrics, the first set of activity metrics corresponding to heart motion when the patient is at rest so that the filtered plurality of activity metrics includes the second set of activity metrics without including the first set of activity metrics, wherein the filtered plurality of activity metrics corresponds to the portion of the accelerometer signal over the first time period;
determining, by the control circuit based on the filtered plurality of activity metrics, a pacing rate; and
causing, by the control circuit, a pulse generator to generate pacing pulses over a second time period at the pacing rate, wherein the second time period occurs after the first time period.

10. The method of claim 9, further comprising determining, by the control circuit, the plurality of activity metrics over the first time period by determining a plurality of activity counts over the first time period.

11. The method of claim 10, further comprising filtering, by the control circuit from the plurality of activity metrics, the first set of activity metrics by filtering a non-zero number of activity counts from the plurality of activity counts, the non-zero number of activity counts corresponding to the heart motion when the patient is at rest.

12. The method of claim 9, further comprising:
identifying, by the control circuit, the first set of activity metrics including each activity metric of the plurality of activity metrics that is less than the threshold such that the first set of activity metrics represents a first percentile of the plurality of activity metrics, and
identifying, by the control circuit, the second set of activity metrics including each of the plurality of activity metrics that is greater than the threshold activity metric such that the second set of activity metrics represents a second percentile of the plurality of activity metric.

13. The method of claim 12, wherein the first percentile is 85%, and wherein the second percentile is 15%.

14. The method of claim 9, further comprising determining, by the control circuit, the pacing rate by determining a lowest pacing rate for pacing the heart.

15. The method of claim 9, wherein the first time period comprises a pacing rate adjustment interval.

16. A non-transitory computer-readable medium configured to store instructions that, when executed, cause one or more processors to:
determine, based on application of one or more thresholds to an accelerometer signal generated by an accelerometer positioned within a housing of an implantable cardiac device, a plurality of activity metrics based on a portion of the accelerometer signal over a first time period, wherein the housing is configured to be implanted within the heart of the patient, wherein each of the plurality of activity metrics indicates an amount of motion of the accelerometer during a respective window of time within the first time period;
identify a first set of activity metrics including each of the plurality of activity metrics that is less than a threshold activity metric, wherein the first set of activity metrics correspond to heart motion when the patient is at rest;
identify a second set of activity metrics including each of the plurality of activity metrics that is greater than the threshold activity metric;
filter, from the plurality of activity metrics, the first set of activity metrics corresponding to heart motion when the patient is at rest so that the filtered plurality of activity metrics includes the second set of activity metrics without including the first set of activity metrics, wherein the filtered plurality of activity metrics corresponds to the portion of the accelerometer signal over the first time period;
determine, based on the filtered plurality of activity metrics, a pacing rate; and
cause a pulse generator to generate pacing pulses over a second time period at the pacing rate, wherein the second time period occurs after the first time period.

17. The implantable cardiac device of claim 1, wherein to filter the first set of activity metrics from the plurality of activity metrics corresponding to heart motion when the patient is at rest, the control circuit is configured to:
set the threshold so that the threshold activity metric represents an upper bound of activity per unit time for when the patient is at rest, and
wherein the control circuit is further configured to:
determine a current amount of activity per unit time;
set the pacing rate at a low pacing rate when the current amount of activity per unit time is less than the threshold activity metric; and
set the pacing rate to be greater than the low pacing rate when the current amount of activity per unit time exceeds the threshold activity metric.

18. The method of claim 9, wherein filtering the first set of activity metrics from the plurality of activity metrics corresponding to heart motion when the patient is at rest comprises:
setting the threshold so that the threshold activity metric represents an upper bound of activity per unit time for when the patient is at rest, and
wherein the method further comprises:
determining, by the control circuit, a current amount of activity per unit time;
setting, by the control circuit, the pacing rate at a low rate unless when the current amount of activity per unit time is less than the threshold activity metric; and setting, by the control circuit, the pacing rate to be greater than the low pacing rate when the current amount of activity per unit time exceeds the threshold activity metric.

19. The implantable cardiac device of claim 17, wherein the control circuit is further configured to:
identify a range of amounts of activity per unit time extending from a first amount of activity per unit time to a second amount of activity per unit time, wherein the range of amounts of activity per unit time correspond to when the patient is engaged in moderate activity; and
set the pacing rate at an activities of daily living (ADL) pacing rate when the current amount of activity per unit time falls within the range of amounts of activity per unit time.

20. The implantable cardiac device of claim 19, wherein the range of amounts of activity per unit time comprises a first range of amounts of activity per unit time, and wherein the control circuit is further configured to:
identify a second range of amounts of activity per unit time extending from a third amount of activity per unit time to a fourth amount of activity per unit time, wherein the range of amounts of activity per unit time correspond to when the patient is engaged in high activity; and
set the pacing rate at a maximum upper pacing rate when the current amount of activity per unit time falls within the second range of amounts of activity per unit time.

* * * * *